(12) United States Patent
Chen et al.

(10) Patent No.: US 11,559,489 B2
(45) Date of Patent: Jan. 24, 2023

(54) TUNING OF RELEASE KINETICS IN HYDROGELS

(71) Applicant: Regeneron Pharmaceuticals, Inc., Tarrytown, NY (US)

(72) Inventors: Hunter Chen, New York, NY (US); Erica Schlesinger, Bend, OR (US); James Feindt, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/541,715

(22) Filed: Aug. 15, 2019

(65) Prior Publication Data

US 2020/0038328 A1    Feb. 6, 2020

Related U.S. Application Data

(63) Continuation of application No. PCT/US2019/040940, filed on Jul. 9, 2019.

(60) Provisional application No. 62/695,472, filed on Jul. 9, 2018.

(51) Int. Cl.

| *A61K 9/06* | (2006.01) |
| *A61K 47/34* | (2017.01) |
| *A61K 9/16* | (2006.01) |
| *C07K 14/47* | (2006.01) |
| *C07K 16/00* | (2006.01) |
| *A61K 38/00* | (2006.01) |

(52) U.S. Cl.
CPC .......... *A61K 9/1682* (2013.01); *A61K 9/1617* (2013.01); *A61K 9/1641* (2013.01); *C07K 14/47* (2013.01); *C07K 16/00* (2013.01); *A61K 38/00* (2013.01); *C07K 2319/32* (2013.01)

(58) Field of Classification Search
None
See application file for complete search history.

(56) References Cited

U.S. PATENT DOCUMENTS

| 4,741,872 A | 5/1988 | De Luca et al. |
| 4,826,945 A | 5/1989 | Cohn et al. |
| 4,938,763 A | 7/1990 | Dunn et al. |
| 5,100,992 A | 3/1992 | Cohn et al. |
| 5,160,745 A | 11/1992 | DeLuca et al. |
| 5,410,016 A | 4/1995 | Hubbell et al. |
| 6,149,931 A | 11/2000 | Schwartz et al. |
| 7,744,913 B2 | 6/2010 | Noyes |
| 9,205,150 B2 | 12/2015 | Jarrett et al. |
| 2013/0071462 A1 | 3/2013 | Jarrett et al. |
| 2013/0156752 A1* | 6/2013 | Jarrett .................... C07K 16/00 424/130.1 |
| 2016/0151535 A1 | 6/2016 | Hoare et al. |
| 2016/0331738 A1* | 11/2016 | Jarrett .................... A61K 31/56 |
| 2017/0258907 A1 | 9/2017 | Kiick et al. |

FOREIGN PATENT DOCUMENTS

| EP | 2389895 A2 | 11/2011 |
| EP | 2708224 A1 | 3/2014 |

* cited by examiner

*Primary Examiner* — Brian Gulledge
(74) *Attorney, Agent, or Firm* — Cooley LLP; Matthew Pavao; Robert E. Powers

(57) ABSTRACT

The present disclosure is directed to methods for tuning the release profile of a biologic disposed in a hydrogel. Parameters that can be used for the tuning include a molar ratio of a nucleophilic group to an electrophilic group, the number of the nucleophilic groups in the first precursor, the number of the electrophilic groups in the second precursor, the molecular weight of the first precursor, the molecular weight of the second precursor, a weight ratio of the biologic and excipient to the hydrogel, a weight percentage of the biologic in a solid state formulation, and a ratio of surface area to volume of the hydrogel. The methods described herein allow the formation of hydrogel with different release profiles suitable for different therapeutic applications.

32 Claims, 16 Drawing Sheets

| Power Analysis | | |
|---|---|---|
| Significance Level | 0.05 | |
| Anticipated RMSE | 1 | |

| Term | Anticipated Coefficient | Power |
|---|---|---|
| Intercept | 1 | 0.896 |
| Mol Ratio | 2 | 1.000 |
| PEG NH Reagent (4-arm) 1 | 2 | 0.971 |
| PEG NH Reagent (4-arm) 2 | 2 | 0.971 |
| PEG NH Reagent (4-arm) 3 | 2 | 0.971 |
| PEG NHS Reagent (4-arm) 1 | 2 | 0.971 |
| PEG NHS Reagent (4-arm) 2 | 2 | 0.971 |
| PEG NHS Reagent (4-arm) 3 | 2 | 0.971 |

| Effect | Power |
|---|---|
| PEG NH Reagent (4-arm) | 1 |
| PEG NHS Reagent (4-arm) | 1 |

FIG. 10

TUNING OF RELEASE KINETICS IN HYDROGELS

CROSS-REFERENCE TO RELATED APPLICATIONS

This application is a Continuation of International Patent Application No. PCT/US2019/040940, filed on Jul. 9, 2019, which claims the benefit of priority to U.S. Provisional Application No. 62/695,472, filed on Jul. 9, 2018, the contents of each of which are hereby incorporated by reference in their entireties.

FIELD OF THE INVENTION

The present invention relates to hydrogels loaded with biologics and methods of tuning the release kinetics in hydrogels.

BACKGROUND OF THE INVENTION

Therapeutic agents require a means of delivery to be effective. Drug delivery relates to administering a pharmaceutical compound to achieve a therapeutic effect in humans or animals. Delivery mechanisms that provide release of an agent over time are useful. Drug delivery technologies can help to modify a drug release profile, absorption, distribution or drug elimination for the benefit of improving product efficacy and safety, as well as patient convenience and compliance.

SUMMARY OF THE INVENTION

One aspect of the present disclosure relates to a method of producing a hydrogel with a desired release profile for a biologic disposed therein, wherein the biologic is in a solid state formulation prior to being disposed in the hydrogel, the method comprising: (i) predetermining at least one of the following parameters: (a) the number of nucleophilic groups in a first precursor; (b) the number of electrophilic groups in a second precursor; (c) the molecular weight of the first precursor; (d) the molecular weight of the second precursor; (e) a weight ratio of the biologic and excipient to the hydrogel; (f) a weight percentage of the biologic in the solid state formulation; and (g) a ratio of surface area to volume of the hydrogel; (ii) determining a molar ratio of the nucleophilic group to the electrophilic group alone, or in combination with any one or more of the above parameters that is not predetermined, until the desired release profile is achieved; and (iii) crosslinking the first precursor and the second precursor at the determined molar ratio around the solid state formulation under anhydrous conditions.

In some embodiments, the molar ratio of the nucleophilic group to the electrophilic group is greater than 1.

In some embodiments, the molar ratio of the nucleophilic group to the electrophilic group is less than 1.

In some embodiments, the molar ratio of the nucleophilic group to the electrophilic group is in the range of about 1.1 to about 2.

In some embodiments, the biologic is a recombinant protein, such as an antibody and a Trap protein (a fusion protein with decoy receptor domains).

In some embodiments, the electrophilic group comprises succinimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole.

In some embodiments, the nucleophilic group comprises a primary amine or a primary thiol.

In some embodiments, the number of the nucleophilic groups in the first precursor is in the range of about 2 to about 10, such as 4 or 8.

In some embodiments, the number of the electrophilic groups in the second precursor is in the range of about 2 to about 10, such as 4 or 8.

In some embodiments, the first precursor comprises (aminopropyl)$_m$ polyoxyethylene, wherein m is in the range of about 2 to about 10.

In some embodiments, the molecular weight of the first precursor is in the range of about 1 kDa to about 100 kDa.

In some embodiments, the second precursor comprises (succinimidyloxyglutaryl)$_n$ polyoxyethylene, wherein n is in the range of about 2 to about 10.

In some embodiments, the molecular weight of the second precursor is in the range of about 1 kDa to about 100 kDa.

In some embodiments, the weight ratio of the biologic to the hydrogel is between about 10% to about 90%. In some embodiments, the weight percentage of the biologic in the solid state formulation is between about 30% to about 95%.

In some embodiments, the method further comprises producing the solid state formulation by spray drying, milling, crystallization, precipitation, spray freezing, super critical fluid drying, electrospraying, or microtemplating.

In some embodiments, the method of producing the solid state formulation is spray drying.

In some embodiments, the solid state formulation comprises particles of ≤20 μm in diameter.

In some embodiments, the desired release profile comprises a release period of about two months to six months for at least 90% biologic release.

In some embodiments, the desired release profile comprises a release period of about one week to two months for at least 90% biologic release.

In some embodiments, the desired release profile exhibits near-linear release over at least one week.

In some embodiments, the desired release profile comprises a delayed-release portion, a sigmoidal shape, a linear portion, a near-linear portion, a logarithmic portion, an exponential portion, or a combination thereof.

In some embodiments, the crosslinking occurs in the presence of an organic solvent that is anhydrous and hydrophobic.

In some embodiments, the organic solvent is methylene chloride, ethyl acetate, dimethyl carbonate, chloroform, or a combination thereof.

In some embodiments, the determining step is performed with a predictive model.

In some embodiments, the molar ratio has a continuous effect on release profile in the predictive model. In some embodiments, the release period in the release profile can be adjusted at a rate of about −41 days per molar ratio change when the molar ratio is greater than 1, e.g., in the range of about 1.3 to about 1.8. In some embodiments, the release period in the release profile can be adjusted at a rate of about 103 days per molar ratio change when the molar ratio is less than 1, e.g., in the range of about 0.77 to about 0.56.

In some embodiments, the molecular weights of the first and second precursors have a non-continuous effect on release profile in the predictive model.

In another aspect, the present disclosure relates to a method of producing a hydrogel having a biologic disposed therein, wherein the biologic is in the solid state formulation prior to being disposed in the hydrogel, and wherein the hydrogel is characterized by a desired release period of about one week to about six months for at least 90% biologic release, the method comprising: (i) selecting a first precursor that comprises two or more nucleophilic groups, wherein the first precursor has a molecular weight in the range of about 1 kDa to about 100 kDa; (ii) selecting a second precursor that comprises two or more electrophilic groups, wherein the second precursor has a molecular weight in the range of about 1 kDa to about 100 kDa; (iii) determining at least one of the following parameters alone, or in combination, until the desired release period is achieved: (a) a molar ratio of the nucleophilic group to the electrophilic group; (b) a weight ratio of the biologic and excipient to the hydrogel; (c) a weight percentage of the biologic in a solid state formulation; and (d) a ratio of surface area to volume of the hydrogel; and (iv) crosslinking the first precursor and the second precursor at the determined molar ratio around the solid state formulation under anhydrous conditions.

In some embodiments, the molar ratio of the nucleophilic group to the electrophilic group is greater than 1.

In some embodiments, the molar ratio of the nucleophilic group to the electrophilic group is less than 1.

In some embodiments, the molar ratio of the nucleophilic group to the electrophilic group is in the range of about 1.1 to about 2.

In some embodiments, the biologic is a recombinant protein, such as an antibody and a Trap protein.

In some embodiments, the electrophilic group comprises succinimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole.

In some embodiments, the nucleophilic group comprises a primary amine or a primary thiol.

In some embodiments, the first precursor comprises about 2 to about 10 nucleophilic groups, such as 4 or 8 nucleophilic groups.

In some embodiments, the second precursor comprises about 2 to about 10 electrophilic groups, such as 4 or 8 electrophilic groups.

In some embodiments, the first precursor comprises (aminopropyl)$_m$ polyoxyethylene, wherein m is in the range of about 2 to about 10.

In some embodiments, the second precursor comprises (succinimidyloxyglutaryl)$_n$ polyoxyethylene, wherein n is in the range of about 2 to about 10.

In some embodiments, the weight ratio of the biologic to the hydrogel is between about 10% to about 90%. In some embodiments, the weight percentage of the biologic in the solid state formulation is between about 30% to about 95%.

In some embodiments, the method further comprises producing the solid state formulation by a method selected from the group consisting of spray drying, milling, crystallization, precipitation, spray freezing, super critical fluid drying, electrospraying, and microtemplating.

In some embodiments, the method of producing the solid state formulation is spray drying.

In some embodiments, the solid state formulation comprises particles of ≤20 μm in diameter.

In some embodiments, the desired release period comprises a release period of about two months to six months for at least 90% biologic release.

In some embodiments, the desired release period comprises a release period of about one week to two months for at least 90% biologic release.

In some embodiments, during the desired release period, the hydrogel produces near-linear release of the biologic.

In some embodiments, the desired release period comprises a delayed-release portion, a sigmoidal shape, a linear portion, a near-linear portion, a logarithmic portion, an exponential portion, or a combination thereof.

In some embodiments, the crosslinking occurs in the presence of an organic solvent that is anhydrous and hydrophobic, such as methylene chloride, ethyl acetate, dimethyl carbonate, chloroform, or a combination thereof.

In some embodiments, the determining step is performed with a predictive model.

In some embodiments, the molar ratio has a continuous effect on release period in the predictive model. In some embodiments, the release period in the release profile can be adjusted at a rate of about −41 days per molar ratio change when the molar ratio is greater than 1, e.g., in the range of about 1.3 to about 1.8. In some embodiments, the release period in the release profile can be adjusted at a rate of about 103 days per molar ratio change when the molar ratio is less than 1, e.g., in the range of about 0.77 to about 0.56.

In some embodiments, the molecular weights of the first and second precursors have a non-continuous effect on release period in the predictive model.

In another aspect, the present disclosure relates to a hydrogel comprising a biologic produced by the methods described herein.

BRIEF DESCRIPTION OF THE DRAWINGS

FIG. 3 illustrates that molecule has minimal impact on release profile. FIGS. 5 and 6 illustrate that increasing surface area to volume ratio has a direct effect on the initial burst release. Therefore, the difference in dissolution phase of the release profiles for the data sets shown in this figure is attributed to the impact of solid loading. The overall effect on the release profile is a result of the combined effect of solid loading and surface area to volume ratio.

FIG. 6 is a graph showing the impact of form factor as described by surface area to volume ratio on release profile, in particular the initial burst release. All protein loaded hydrogels shown in this figure contain 40 kDa PEG-NHS HGEO and 15 kDa PEG-NH HGEO PEG components, mAb IgG1, 80% protein content, 80% solid loading, and 1.7 molar ratio with low surface area to volume ratio in slab form, 12 mm$^{-1}$ (squares), or high surface area to volume ratio in the form of microparticles, >30 mm$^{-1}$ (diamonds).

FIG. 10 shows model analysis for the study performed in Example 2. Power >0.95 with AC<6 indicate strong predictive power of model.

FIGS. 16-17 show that the same release period can be targeted by selecting different combinations of PEG reagents and molar ratios.

FIGS. 18-19 show that by adjusting both the molar ratio and PEG reagents, release periods from about 8 to 59 days can be achieved.

FIGS. 18 and 20 show that by adjusting the molar ratio only, release periods within an allowable range for a given PEG combination can be targeted.

FIGS. 21 and 22 show that the same release period can be targeted by selecting different combinations of PEG reagents and molar ratios.

DETAILED DESCRIPTION OF THE INVENTION

Figure 1:
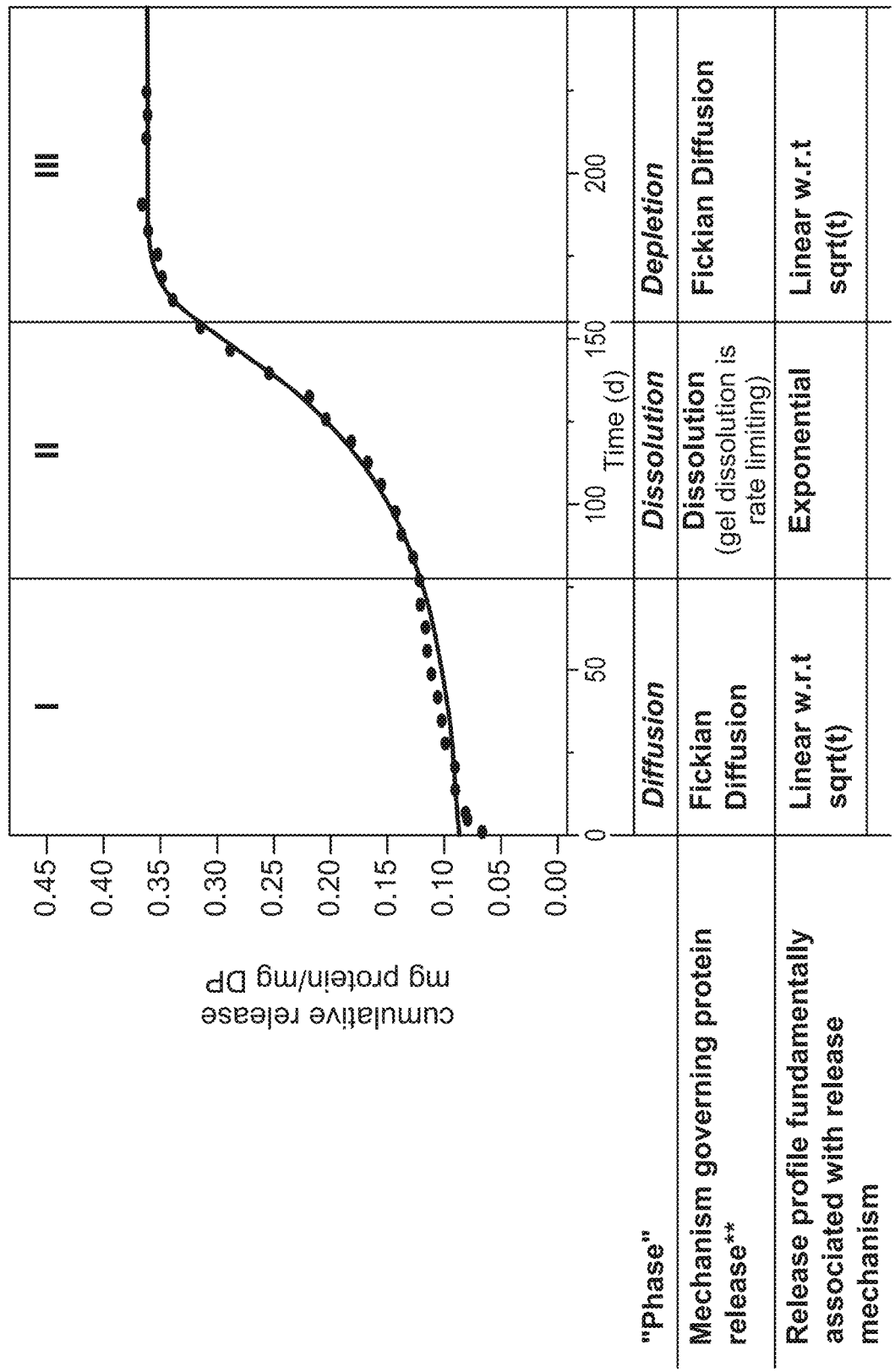
FIG. 1 is a schematic explaining the characteristic sigmoidal release profile of a monoclonal antibody (mAb) from a hydrogel.

Cross-linked PEG hydrogels encapsulating micronized, solid-state proteins have shown promise for sustained release on the order of weeks or months with good protein stability. Based on demonstrated loading capacities up to 88% w/w total solid loading, this approach is feasible for both low and medium dose molecules with durations on the order of months, e.g., about 1 week to 6 months. In efforts to develop this system as a platform delivery system tunable for sustained release suitable for a variety of target product profiles, important formulation parameters impacting release kinetics have been identified and explored in multi-factorial studies. A method for non-linear modeling of release profiles that captures the shape typical of degradable hydrogel release profiles is introduced and utilized in evaluating the impact of formulation parameters on protein release.

The present invention is based in part on the discovery that the following parameters are important in affecting the release profile of a biologic disposed in a hydrogel: (a) a molar ratio of a nucleophilic group to an electrophilic group, wherein a first precursor comprises two or more nucleophilic groups and a second precursor comprises two or more electrophilic groups; (b) the number of the nucleophilic groups in the first precursor; (c) the number of the electrophilic groups in the second precursor; (d) the molecular weight of the first precursor; (e) the molecular weight of the second precursor; (f) a weight ratio of the biologic and excipient to the hydrogel; (g) a weight percentage of the biologic in a solid state formulation; and (h) a ratio of surface area to volume of the hydrogel. By adjusting at least one of these parameters while the other parameters are predetermined, one can produce an array of biologic-loaded hydrogel formulations with different release profiles.

In some embodiments, a quantitative, predictive model can be used to determine these parameters for a desired release profile. For example, using the predictive model, one can predetermine one or more of the above-mentioned parameters, and adjust one or more parameter of interest to evaluate its effect on the release profile. The parameter of interest can be adjusted until the desired release profile is achieved. Among other things, the predictive model offers the ability to: (1) target the same release period by selecting different combinations of precursors and molar ratios; (2) target release periods, e.g., from 8-59 days, by adjusting both the molar ratio and precursors; and (3) target release periods within an allowable range for a given precursor combination by adjusting the molar ratio only.

One aspect of the present disclosure relates to a method of producing a hydrogel with a desired release profile for a biologic disposed therein, wherein the biologic is in a solid state formulation prior to being disposed in the hydrogel, the method comprising: (i) predetermining at least one of the following parameters: (a) the number of nucleophilic groups in a first precursor; (b) the number of electrophilic groups in a second precursor; (c) the molecular weight of the first precursor; (d) the molecular weight of the second precursor; (e) a weight ratio of the biologic and excipient to the hydrogel; (f) a weight percentage of the biologic in the solid state formulation; and (g) a ratio of surface area to volume of the hydrogel; (ii) determining a molar ratio of the nucleophilic group to the electrophilic group alone, or in combination with any one or more of the above parameters that is not predetermined, until the desired release profile is achieved; and (iii) crosslinking the first precursor and the second precursor at the determined molar ratio around the solid state formulation under anhydrous conditions.

Another aspect of the present disclosure relates to a method of producing a hydrogel having a biologic disposed therein, wherein the biologic is in a solid state formulation prior to being disposed in the hydrogel, and wherein the hydrogel is characterized by a desired release period of about one week to about six months for at least 90% biologic release, the method comprising: (i) selecting a first precursor that comprises two or more nucleophilic groups, wherein the first precursor has a molecular weight in the range of about 1 kDa to about 100 kDa; (ii) selecting a second precursor that comprises two or more electrophilic groups, wherein the second precursor has a molecular weight in the range of about 1 kDa to about 100 kDa; (iii) determining at least one of the following parameters alone, or in combination, until the desired release period is achieved: (a) a molar ratio of the nucleophilic group to the electrophilic group; (b) a weight ratio of the biologic and excipient to the hydrogel; (c) a weight percentage of the biologic in the solid state formulation; and (d) a ratio of surface area to volume of the hydrogel; and (iv) crosslinking the first precursor and the second precursor at the determined molar ratio around the solid state formulation under anhydrous conditions.

The precursors are not the hydrogels but can be cross-linked with each other to form the hydrogel. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that can react with each other to form matrices and/or polymers made of repeating units. Precursors may be polymers.

To form covalently crosslinked hydrogels, the precursors are covalently crosslinked together. In general, polymeric precursors are polymers that will be joined to other polymeric precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., the contents of each of which are hereby incorporated by reference herein in their entireties to the extent they do not contradict what is explicitly disclosed herein.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

The precursors may have biologically inert and hydrophilic portions, e.g., a core. In the case of a branched polymer, a core refers to a contiguous portion of a molecule joined to arms that extend from the core, with the terminus of each arm having a functional group. A hydrophilic precursor or precursor portion has a solubility of at least 1 g/100 mL in an aqueous solution. A hydrophilic portion may be, for instance, a polyether, for example, polyalkylene oxides such as polyethylene glycol (PEG), polyethylene oxide (PEO), polyoxyethylene, polyethylene oxide-co-polypropylene oxide (PPO), co-polyethylene oxide block or random copolymers, and polyvinyl alcohol (PVA), poly (vinyl pyrrolidone) (PVP), poly(amino acids), dextran, or a protein. The precursors may have a polyalkylene glycol portion and may be polyethylene glycol based, with at least about 80% or 90% by weight of the polymer comprising polyethylene oxide repeats. The polyethers and more particularly poly(oxyalkylenes) or poly(ethylene glycol) or polyethylene glycol are generally hydrophilic. As is customary in these arts, the term PEG is used to refer to PEO with or without hydroxyl end groups.

Precursors may be made with a hydrophobic portion provided that the resultant hydrogel retains the requisite amount of water. In some cases, the precursor is nonetheless soluble in water because it also has a hydrophilic portion. In other cases, the precursor makes dispersion in the water (a suspension) but is nonetheless able to react to from a crosslinked material. Some hydrophobic portions may include a plurality of alkyls, polypropylenes, or other groups. Some precursors with hydrophobic portions are sold under the trade names PLURONIC® F68, JEFFAMINE®, or TECTRONIC®. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees centigrade.

Precursors may have a plurality of arms, e.g., 2-100 arms, with each arm having a terminus, bearing in mind that some precursors may be dendrimers or other highly branched materials. The terminus of each arm can include a nucleophilic or electrophilic group. An arm on a hydrogel precursor refers to a linear chain of chemical groups that connect a cross-linkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

In some embodiments, the first precursor can comprise about 2-30 nucleophilic groups, e.g., about 2-25, about 2-20, about 2-15, about 2-10, about 5-30, about 5-25, about 5-20, or about 5-15 nucleophilic groups. In some embodiments, the first precursor comprises about 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleophilic groups.

In some embodiments, the second precursor can comprise about 2-30 electrophilic groups, e.g., about 2-25, about 2-20, about 2-15, about 2-10, about 5-30, about 5-25, about 5-20, or about 5-15 electrophilic groups. In some embodiments, the second precursor comprises about 2, 3, 4, 5, 6, 7, 8, 9, 10, 11, 12, 13, 14, 15, 16, 17, 18, 19, 20, 21, 22, 23, 24, 25, 26, 27, 28, 29, or 30 electrophilic groups.

Thus hydrogels can be made, e.g., from a multi-armed precursor with a first set of functional groups and another multi-armed precursor having a second set of functional groups. For example, a six-armed or eight-armed precursor may have hydrophilic arms, e.g., polyethylene glycol, terminated with primary amines, with the molecular weight of the arms being about 1,000 to about 40,000 Daltons (Da); artisans will immediately appreciate that all ranges and values within the explicitly stated bounds are contemplated. Such precursors may be mixed with relatively smaller precursors, for example, molecules with a molecular weight of between about 100 Da and about 5000 Da, or no more than about 800 Da, 1000 Da, 2000 Da, or 5000 Da having at least about three functional groups, or between about 3 to about 16 functional groups; ordinary artisans will appreciate that all ranges and values between these explicitly articulated values are contemplated. Such small molecules may be polymers or non-polymers and natural or synthetic.

In some embodiments, the precursors can be dendrimers. Dendrimers are highly branched, radially symmetrical polymers in which the atoms are arranged in many arms and subarms radiating out from a central core. In some embodiments, the precursors are not dendrimers.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls).

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 Da MW polyethylene glycol has enough $CH_2CH_2O$ groups to total at least 1000 Da MW. As is customary terminology in these arts, a polyethylene glycol polymer does not necessarily refer to a molecule that terminates in a hydroxyl group. Molecular weights are abbreviated in thousands using the symbol k, e.g., with 15 k Da meaning 15,000 Da molecular weight. Succinimidyl succinate, succinimidyl glutarate, succinimidyl adipate, and succinimidyl azelate are succinimidyl esters that have an ester group that degrades by hydrolysis in water. Hydrolytically degradable thus refers to a material that would spontaneously degrade in vitro in an excess of water without any enzymes or cells present to mediate the degradation. A time for degradation refers to effective disappearance of the material as judged by the naked eye. PEG and/or hydrogels, as well as compositions that comprise the same, may be provided in a form that is pharmaceutically acceptable, meaning that it is highly purified and free of contaminants, e.g., pyrogens.

Non-limiting examples of nucleophilic groups include amine, hydroxyl, carboxyl, and thiol. In some embodiments, the nucleophilic group is amine. The amine can be a primary amine, a secondary amine, a tertiary amine, or a cyclic amine. In some embodiments, the first precursor comprises (aminopropyl)$_m$ polyoxyethylene, wherein m is in the range of about 2 to about 10. For example, m is 2, 3, 4, 5, 6, 7, 8, 9, or 10. In some embodiments, the first precursor can be pentaerythritol tetra(aminopropyl) polyoxyethylene, hexaglycerol octa(aminopropyl) polyoxyethylene, or a combination thereof. The molecular weight of the first precursor can be in the range of about 1 kDa to about 100 kDa, e.g., about 5 kDa to about 100 kDa, about 10 kDa to about 100 kDa, or about 20 kDa to about 100 kDa.

Non-limiting examples of electrophilic groups include sulfonyl chloride, chlorocarbonates, n-hydroxysucciniinidyl ester, succinimidyl ester, sulfasuccinimidyl esters, succinimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole, and those disclosed in U.S. Pat. Nos. 5,410,016 and 6,149,931, each of which are hereby incorporated by reference herein in its entirety to the extent they do not contradict what is explicitly disclosed herein. In some embodiments, the electrophilic group is n-hydroxysucciniinidyl ester or n-hydroxysuccinimide. In some embodiments, the second precursor comprises (succinimidyloxyglutaryl)$_n$ polyoxyethylene, wherein n is in the range of about 2 to about 10. For example, n is 2, 3, 4, 5, 6, 7, 8, 9, or 10. In some embodiments, the second precursor can be pentaerythritol tetra(succinimidyloxyglutaryl) polyoxyethylene, pentaerythritol tetra(succinimidyloxysuccinyl) polyoxyethylene, pentaerythritol tetra(succinimidyl carboxypentyl) polyoxyethylene, hexaglycerol octa(succinimidyloxyglutaryl) polyoxyethylene, hexaglycerol octa(succinimidyloxysuccinyl) polyoxyethylene, or a combination thereof. The molecular weight of the second precursor can be in the range of about 1 kDa to about 100 kDa, e.g., about 5 kDa to about 100 kDa, about 10 kDa to about 100 kDa, or about 20 kDa to about 100 kDa.

In some embodiments, the electrophilic group is n-hydroxysucciniinidyl ester or n-hydroxysuccinimide, and the nucleophilic group is primary amine.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfasuccinimidyl esters, N-hydroxysuccinimidyl ester, succinimidyl ester, epoxide, aldehyde, maleimides, imidoesters and the like.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a Michael-type reaction. The strong electrophile may be of a type that does not participate in a Michael-type reaction or of a type that participates in a Michaels-type reaction. Examples of strong electrophiles that do not participate in a Michael-type reaction are: succinimides, succinimidyl esters, or NHS-esters. Examples of Michael-type electrophiles are acrylates, methacrylates, methylmethacrylates, and other unsaturated polymerizable groups. More embodiments of the precursors and functional groups can be found at U.S. Pat. No. 9,205,150, the contents of which are incorporated by reference in their entities.

Figure 2:
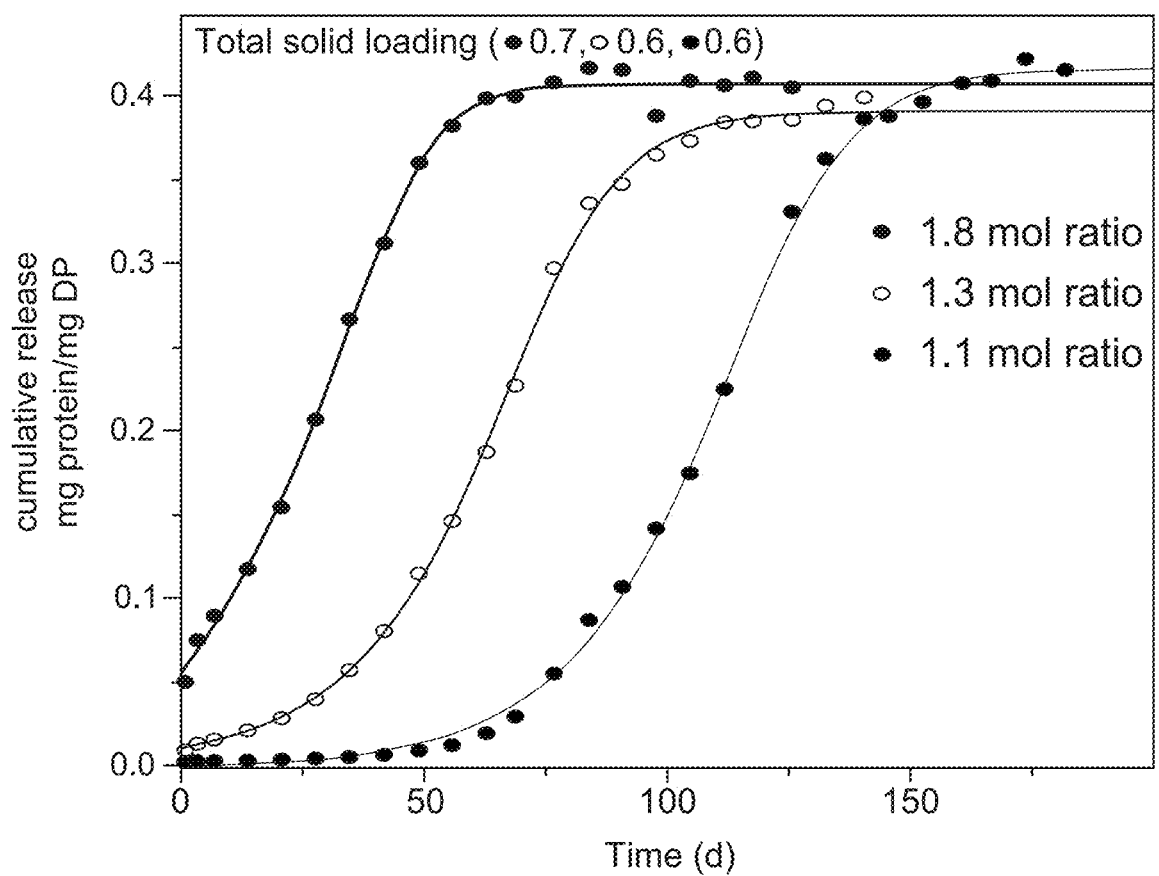
FIG. 2 is a graph showing the impact of molar ratio on release profile. Experimental release profiles are fit with a Logistic 5 parameter (L5P) curve. All protein loaded crosslinked PEG (XPEG) hydrogels shown in this figure are mAb IgG1-XPEG with 81.9% w/w protein content in the spray dried formulation, 40 kDa PEG-NHS HGEO and 15 kDa PEG-NH HGEO PEG components, with molar ratios of 1.1, 1.3, and 1.8 and solid loadings of 60%, 60%, and 70% respectively.
Figure 3:
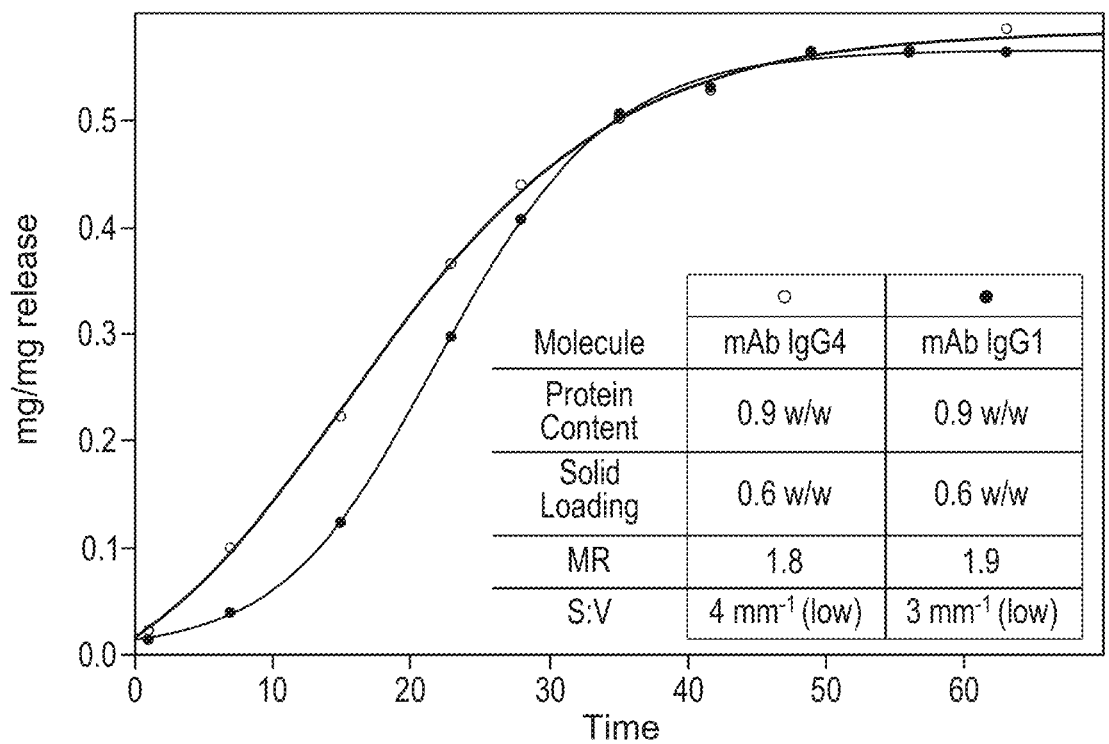
FIG. 3 is a graph showing that molecule has minimal impact on release profile. Experimental release profiles are fit with an L5P curve. All protein loaded hydrogels shown in this figure contain spray dried formulations with 90% w/w protein content, 40 kDa PEG-NHS HGEO and 15 kDa PEG-NH HGEO PEG components, 60% w/w solid loading, molar ratios around 1.8-1.9, and surface area to volume ratios around 3 mm$^{-1}$-4 mm$^{-1}$. Release from mAb IgG4-XPEG is shown in open circles, and release from mAb IgG1-XPEG is shown in closed circles. As both mAbs are similar in size, the primary property impacting diffusion through a porous matrix, it is expected that release kinetics from the hydrogel will be molecule independent.

The molar ratio of the nucleophilic group to the electrophilic group can determine the crosslink density. A molar ratio of one results in the highest crosslink density. A molar ratio of greater or less than one can lead to lower crosslink density than a molar ratio of one. The crosslink density increases as the molar ratio increases until it reaches the value of one, then the crosslink density decreases as the molar ratio increases beyond the value of one. The biologic embedded in the hydrogel can be released faster when the crosslink density is lower. For example, see the results shown in FIG. 2. As a result, by adjusting the molar ratio of the nucleophilic group to the electrophilic group, one can tune the release kinetics of the biologic. Without wishing to be bound by theory, the molar ratio effectively modulates both the crosslink density (i.e. number of covalent crosslinks forming the network) and the network pore size within the hydrogel matrix. By decreasing the crosslink density, the effective pore size of the matrix can be increased, resulting in faster diffusion of protein through the matrix. Additionally, decreasing crosslink density can increase domains in the hydrogel where the local concentration of PEG surrounding the protein particle is insufficient to retain protein in the solid state upon hydration, leading to an increase in burst release as well as the rate of diffusion on a mass basis. Thus it is expected that as molar ratio increases, both burst release and release kinetics in the diffusion controlled regime will increase. Additionally, there is an observed increase in the slope of the release profile in the dissolution-controlled regime with increasing molar ratio. This can be explained by the reduction in the extent of cross-linking with increasing molar ratio as there is a greater mismatch between the number of nucleophilic groups and electrophilic groups available to react and crosslink. The growth rate is determined by the rate of hydrolysis of the crosslinks, leading to an increase in hydrogel swelling and a concomitant decrease in local concentrations of PEG that result in additional dissolution of protein particles. Swelling of the hydrogel is also correlated with hydrogel porosity, which is increased as protein dissolution occurs. As molar ratio increases and protein dissolution upon hydration increases, so will the effective porosity of the hydrogel, leading to more swelling, a faster hydrolysis, and faster growth rate in the dissolution-controlled regime. Furthermore, the inflection point identifying the transition between diffusion and dissolution-controlled regimes will be inversely correlated with molar ratio. As effective rates of diffusion increase with increasing molar ratio, the time it takes for diffusion to increase to the extent that it is no longer the rate-limiting step decreases, and thereby shifts the inflection point to earlier time points. Considered comprehensively, varying the molar ratio alone can permit the release profile to be tuned from near linear to sigmoidal depending on the desired result.

In some embodiments, the molar ratio of the nucleophilic group to the electrophilic group is greater than 1. In some embodiments, the molar ratio of the nucleophilic group to the electrophilic group is less than 1. In some embodiments, the molar ratio of the nucleophilic group to the electrophilic group can be in the range of about 0.1 to 3.0, e.g., about 0.1 to 0.9, about 0.1 to 0.8, about 0.1 to 0.7, about 0.1 to 0.6, about 0.2 to 0.9, about 0.2 to 3.0, about 0.2 to 2.8, about 0.2 to 2.5, about 0.5 to 2.5, about 0.5 to 2.0, about 0.8 to 2.5, about 0.8 to 2.0, about 1.1 to 2.0, about 1.1 to 2.5, about 1.1 to 3.0, about 1.5 to 3.0, about 1.5 to 2.5, about 1.5 to 2.0, or about 1.3 to 1.8. In some embodiments, the molar ratio of the nucleophilic group to the electrophilic group can be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In some embodiments, the molar ratio of the nucleophilic group to the electrophilic group is not 1.

In the predictive model, the molar ratio has a continuous effect on release profile. As used herein, the term "continuous" means that one can interpolate between levels. As such, molar ratios can be adjusted continuously to give incremental variation in release periods. In some embodiments, the release period in the release profile can be adjusted at a rate of about −41 days per molar ratio change when the molar ratio is greater than 1, e.g., in the range of about 1.3 to about 1.8. In some embodiments, the release period in the release profile can be adjusted at a rate of about 103 days per molar ratio change when the molar ratio is less than 1, e.g., in the range of about 0.77 to about 0.56.

Related to the molar ratio, the number of the nucleophilic group in the first precursor and/or the number of the electrophilic group in the second precursor can also determine the crosslink density. Generally, at a given molar ratio, the higher the number of the nucleophilic or electrophilic group, the higher the crosslink density. In some embodiments, the method comprises selecting 8-arm PEG NH and 8-arm PEG NHS reagents for a release period of 60 days or longer. In some embodiments, the method comprises selecting 4-arm PEG NH and 4-arm PEG NHS reagents for a release period of less than 60 days.

Another parameter that one can use to tune the release kinetics is the molecular weight of the first and/or second precursor. At a given molar ratio, the lower the molecular weight of the precursor, the smaller the network pore size. The molecular weights of the first and second precursors have a non-continuous or discrete effect on release profile in the predictive model described herein. As used herein, the term "non-continuous" or "discrete" means that one cannot interpolate between levels. For example, a combination of first and second precursors (e.g., PEG reagents) with predetermined molecular weights can define a range of release periods possible. Other factors such as molar ratio can be used to fine tune the release profile or release period. For example, as shown in Table 9, a combination of 10 kDa PEG NH and 15 kDa PEG NHS defines a release period in the range of 9-31 days; by varying the molar ratio in the range of 1.3 and 1.8, one can continuously tune the release period from 31 days to 9 days. In the predictive model, the molar ratio, molecular weight of the first precursor, and molecular weight of the second precursor are independent parameters.

In some embodiments, the method comprises: (a) selecting a range of molar ratios defined by a first molar ratio as minimum and a second molar ratio as maximum, and the molecular weights of the first and the second precursors, thereby resulting in a range of release periods defined by a first release period as maximum and a second release period as minimum, wherein the first molar ratio is 1 or greater, and wherein the desired release period is within the range of release periods; and (b) determining the desired molar ratio in accordance with either one of the following formulae:

Desired molar ratio=First molar ratio+(First release period−Desired release period)/41; and Desired molar ratio=Second molar ratio+(Second release period−Desired release period)/41.

In some embodiments, the range of molar ratios is about 1.3 to about 1.8 or a subrange thereof. In some embodiments, the first molar ratio can be about 1.3, and the second molar ratio can be greater than about 1.3 and no more than about 1.8, e.g., about 1.4, about 1.5, about 1.6, about 1.7, or about 1.8. In some embodiments, the first molar ratio can be about 1.4, and the second molar ratio can be greater than about 1.4 and no more than about 1.8, e.g., about 1.5, about 1.6, about 1.7, or about 1.8. In some embodiments, the first molar ratio can be about 1.5, and the second molar ratio can be greater than about 1.5 and no more than about 1.8, e.g., about 1.6, about 1.7, or about 1.8. In some embodiments, the first molar ratio can be about 1.6, and the second molar ratio can be greater than about 1.6 and no more than about 1.8, e.g., about 1.7 or about 1.8. In some embodiments, the first molar ratio can be about 1.7, and the second molar ratio can be greater than about 1.7 and no more than about 1.8, e.g., about 1.8.

In some embodiments, the method comprises: (a) selecting a range of molar ratios defined by a first molar ratio as maximum and a second molar ratio as minimum, and the molecular weights of the first and the second precursors, thereby resulting in a range of release periods defined by a first release period as maximum and a second release period as minimum, wherein the first molar ratio is 1 or less, and wherein the desired release period is within the range of release periods; and (b) determining the desired molar ratio in accordance with either one of the following formulae:

Desired molar ratio=First molar ratio−(First release period−Desired release period)/103; and Desired molar ratio=Second molar ratio−(Second release period−Desired release period)/103.

In some embodiments, the range of molar ratios is about 0.77 to about 0.56 or a subrange thereof. In some embodiments, the first molar ratio can be about 0.77, and the second molar ratio can be less than about 0.77 and no less than about 0.56, e.g., about 0.7, about 0.65, about 0.6, or about 0.56. In some embodiments, the first molar ratio can be about 0.7, and the second molar ratio can be less than about 0.7 and no less than about 0.56, e.g., about 0.65, about 0.6, or about 0.56. In some embodiments, the first molar ratio can be about 0.65, and the second molar ratio can be less than about 0.65 and no less than about 0.56, e.g., about 0.6 or about 0.56. In some embodiments, the first molar ratio can be about 0.6, and the second molar ratio can be less than about 0.6 and no less than about 0.56, e.g., about 0.56.

Figure 5:
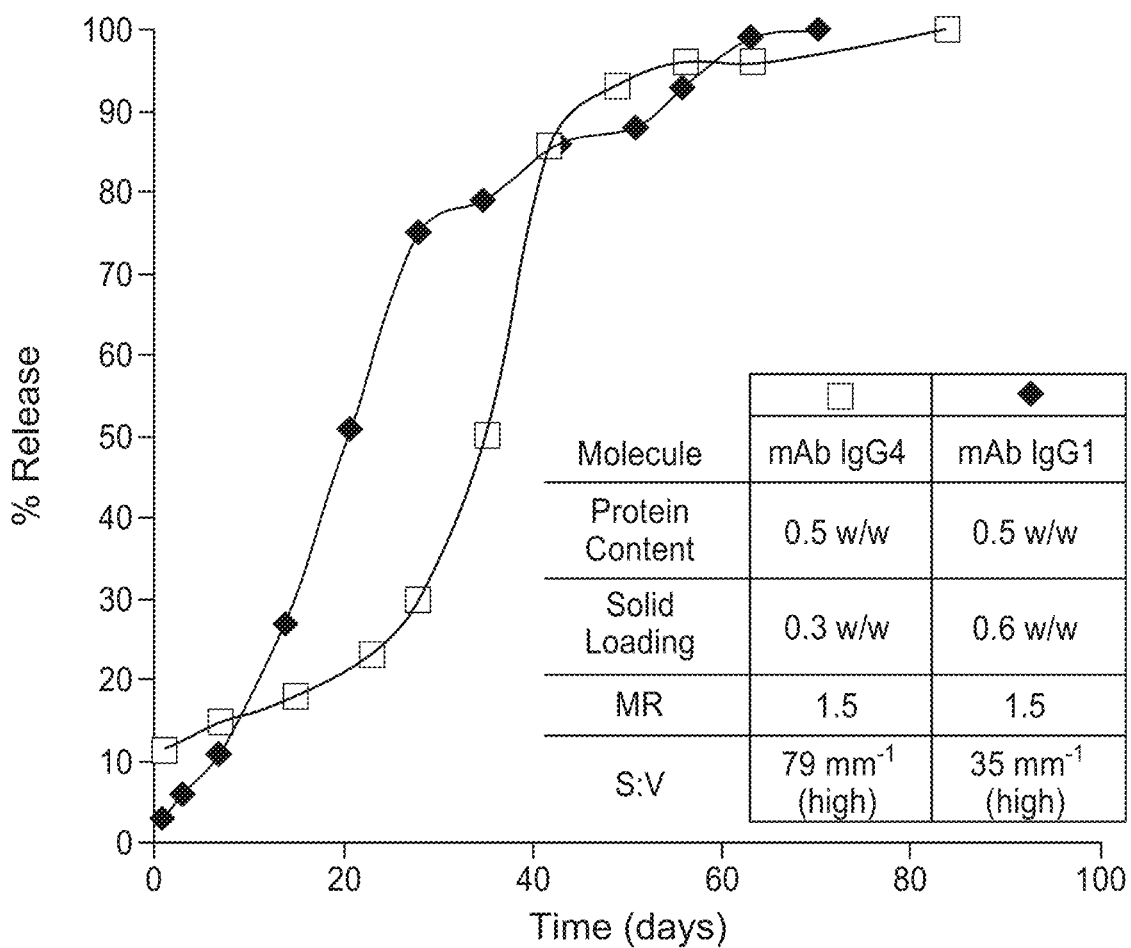
FIG. 5 is a graph showing the impact of solid loading on release profile. All protein loaded hydrogels shown in this figure contains 1.5 molar ratio, 40 kDa PEG-NHS HGEO and 15 kDa PEG-NH HGEO PEG components, and 50% protein content with mAb IgG4, 30% solid loading, and 79 mm$^{-1}$ surface area to volume ratio (squares) or mAb IgG1, 60% solid loading, and 35 mm$^{-1}$ surface area to volume ratio (diamonds).

Another parameter that one can use to tune the release kinetics is a weight ratio of the biologic and excipient to the hydrogel. The weight ratio of the biologic and excipients to the hydrogel is also referred to herein as "solid loading." This refers to the weight ratio of the biologic and excipient to the total weight of the biologic, excipient, and polymer comprising the protein-loaded hydrogel. It was discovered that increasing the solid loading can change the shape of the release profile, primarily due to faster release during the initial diffusion phase before the inflection point. There is also likely an inverse correlation between the onset of the dissolution phase (i.e. the inflection point) and the solid loading. Without wishing to be bound by theory, with increased solid loading, faster release during the initial diffusion phase is expected because there will be a larger quantity of protein in microenvironments of relatively low PEG concentration where protein solubility is less limited. Protein in such regions will be dissolved upon initial hydration of the matrix, increasing the rate of concentration-dependent diffusion. Additionally, the increase in protein particles dissolved upon initial hydration will create voids within the matrix and lead to an increase in matrix porosity. A more porous matrix will also increase the effective rate of diffusion through the bulk matrix and released as it reaches the surface. Without wishing to be bound by theory, the inverse correlation between inflection point and solid loading can also be hypothetically explained by the increase in rate of diffusion observed with increased solid loading. The inflection point signifies the transition between a diffusion-controlled regime and a dissolution-controlled regime. As solid loading increases, the diffusion rate starts higher and increases more rapidly, leading to a shorter duration before diffusion is no longer rate limiting. In the diffusion-controlled regime, diffusion of dissolved protein through the matrix is the rate-limiting step for protein release. As more protein particles dissolve, voids within the matrix are created and the porosity of the matrix increases, leading to increased rates of diffusion. In the dissolution-controlled regime, diffusion through the matrix is no longer the rate-limiting step. This point is reached more rapidly as solid loading increases. For example, FIG. 5 illustrates the effects of solid loading on the release rate and profile.

In some embodiments, the biologic can be a peptide or protein, such as a recombinant protein. The recombinant protein can be an antibody or fragment thereof, a short chain variable fragment (scFv), a growth factor, an angiogenic factor, or insulin. Other water soluble biologics are carbohydrates, polysaccharides, nucleic acids, antisense nucleic acids, RNA, DNA, small interfering RNA (siRNA), and aptamers. In some embodiments, the biologic is an anti-vascular endothelial growth factor agent such as aflibercept, bevacizumab, and ranibizumab. In some embodiments, the biologic is an immunoglobulin G such as IgG1, IgG2, IgG3, and IgG4. In some embodiments, the biologic is a bispecific monoclonal antibody. There are many formats of bispecific monoclonal antibody, but the two main categories are IgG-like and non-IgG-like. In some embodiments, the biologic is a fusion protein with decoy receptor domains.

The water-soluble biologics can be prepared as particles before dispersal into the hydrogels. Multiple protein particulation technologies, such as spray drying or precipitation exist and may be employed provided the protein of interest is compatible with such processing. An embodiment of particle preparation involves receiving the biologic without substantial denaturation, e.g., from a supplier or animal or recombinant source. The solid phase is a stable form for the protein. The protein is lyophilized or concentrated or used as received. The protein is then prepared as a fine powder without denaturation by processing it in a solid state and avoiding high temperatures, moisture, and optionally in an oxygen free environment. Powders may be prepared by, for example, spray drying, grinding, ball milling, cryomilling, microfluidizing or mortar-and-pestle followed by sieving a solid protein. The protein may also be processed in a compatible anhydrous organic solvent in which the protein in question is not soluble, while keeping the protein in a solid form. Particle size reduction to the desired range may be achieved by, for example, grinding, ball milling, jet milling of a solid protein suspension in a compatible organic solvent.

Common excipients include, but are not limited to, sucrose, proline, trehalose, trileucine, mannitol, isoleucine, buffers such as histidine, phosphate, acetate, and polysorbates.

The solid loading can be in the range of 0.1 to 0.9, e.g., 0.1-0.8, 0.1-0.7, 0.1-0.6, 0.2-0.9, 0.2-0.8, 0.2-0.7, 0.2-0.6, 0.3-0.9, 0.3-0.8, 0.3-0.7, or 0.3-0.6. In some embodiments, the solid loading can be about 0.1, 0.2, 0.3, 0.4, 0.5, 0.6, 0.7, 0.8, or 0.9.

Figure 4:
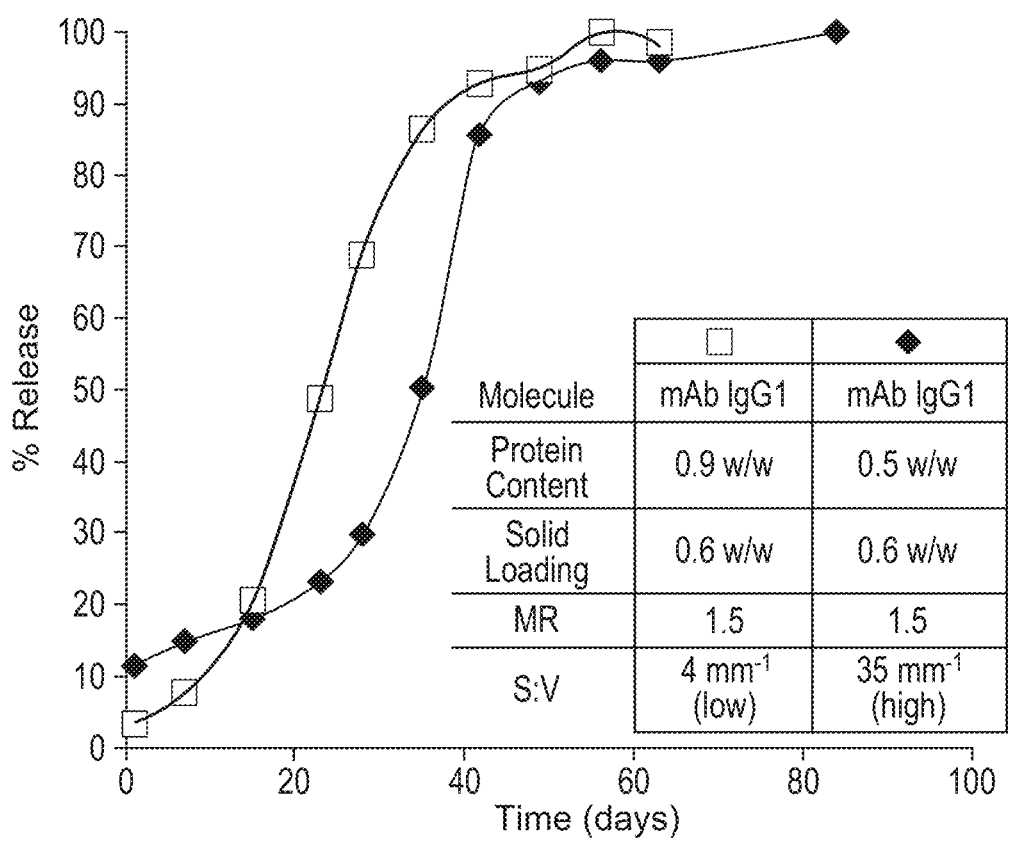
FIG. 4 is a graph showing the impact of protein content in the spray dried formulation on release profile. All protein loaded hydrogels shown in this figure contains mAb IgG1, 60% loading, 1.5 molar ratio, and 40 kDa PEG-NHS HGEO and 15 kDa PEG-NH HGEO PEG components with 90% w/w protein content and 4 mm$^{-1}$ surface area to volume ratio (squares) or 50% w/w protein content and 35 mm$^{-1}$ surface area to volume ratio (diamonds). Data have not been normalized for surface area to volume ratio, however by comparing this data set with FIG. 6, it is clear that the observed difference in release profile is not attributed to the surface area to volume ratio alone as the trends are opposite. Thus, the observed difference in this data set is attributed to the protein content in the spray dried formulation and/or a combined effect of surface area to volume ratio and the protein content in the spray dried formulation.

Yet another parameter that one can use to tune the release kinetics is the weight percentage of the biologic in a solid state formulation. A solid state formulation described herein is compositionally different from a dehydrated hydrogel of the present disclosure. The dehydrated hydrogel is formed by crosslinking a first precursor and a second precursor around the solid state formulation. The weight percentage of the biologic in a solid state formulation is also referred to herein as "protein content." It was discovered that the higher the protein content, the faster the rate of release. In addition, the protein content can also impact the release profile shape by changing the inflection point and release rate up to the inflection point. The protein content of the micronized particle can determine the effective concentration of protein in the microenvironment upon dissolution of the particle within the matrix. Diffusion within the PEG hydrogel is driven by such concentration gradients within the microenvironments throughout the matrix. Thus, for solid state formulations with high protein content, the local concentrations upon dissolution will be higher than for formulations with low protein content, which creates a greater driving force for diffusion. This is observed by the correlation between the rate of release in the diffusion-controlled regime prior to the inflection point and protein content. Without wishing to be bound by theory, the inverse correlation between the inflection point and the protein content can be explained by reducing the time frame in which the concentration-dependent diffusion rate increases and dissolution becomes the rate-limiting step for release. For example, FIG. 4 illustrates the effects of protein content on the release rate and profile.

The solid state formulation comprises the biologic and one or more excipients. The solid state formulation can be produced by methods such as precipitation, crystallization, lyophilizing, spray drying, milling, microtemplating, spray freezing, reversible precipitation, super critical fluid drying, and electrospraying. Lyophilized, spray dried or otherwise processed proteins are often formulated with sugars such as trehalose or sucrose to stabilize the protein or other processes used to prepare the proteins. These sugars may be allowed to persist in the particle throughout the hydrogel formation process. The protein content can be in the range of 10% to 95% by weight, e.g., 10%-90%, 10%-80%, 10%-70%, 10%-60%, 20%-90%, 20%-80%, 20%-70%, 30%-90%, 30%-80%, or 30%-70% by weight. In some embodiments, the protein content can be about 10%, 20%, 30%, 40%, 50%, 60%, 70%, 80%, or 90% by weight.

The solid state formulation can include particles having an average diameter no more than 20 µm. In some embodiments, the solid state formulation can include particles having an average diameter of about 10 nm to 20 µm. For example, the particles can have an average diameter of about 10 nm to 15 µm, 10 nm to 10 µm, 50 nm to 20 µm, 50 nm to 15 µm, 50 nm to 10 µm, 100 nm to 15 µm, 100 nm to 10 µm, 200 nm to 10 µm, 400 nm to 10 µm, 600 nm to 10 µm, 1 µm to 10 µm, 2 µm to 10 µm, 100 nm to 1 µm, or 200 nm to 800 nm.

Figure 6:
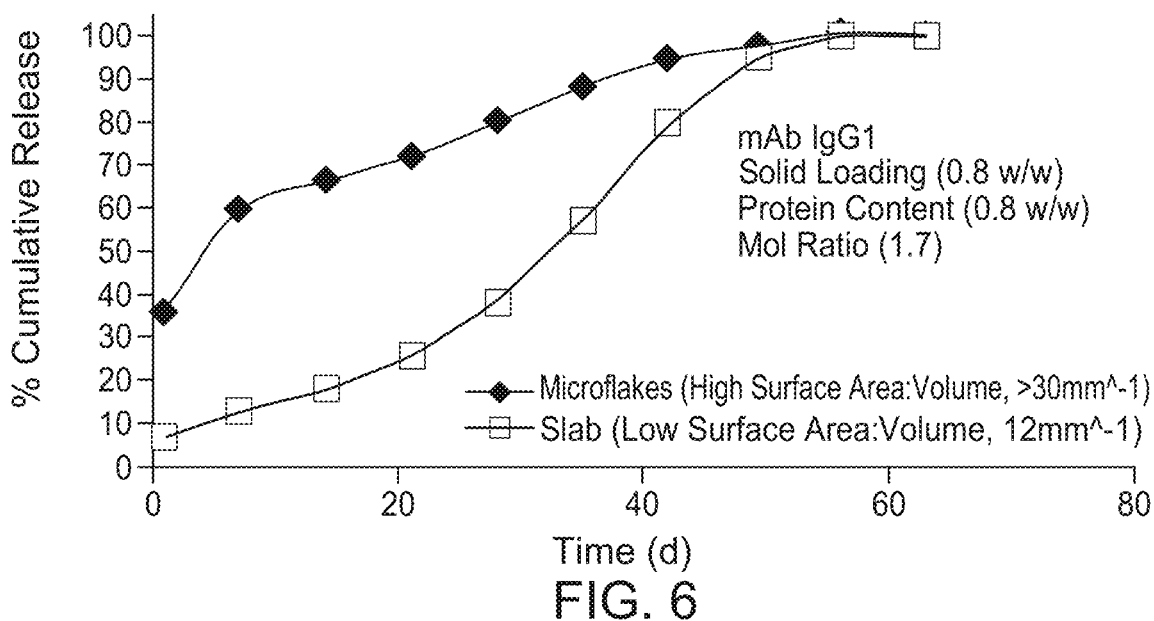

Yet another parameter that one can use to tune the release kinetics is the ratio of surface area to volume of the hydrogel. It was discovered that the higher the ratio of surface area to volume, the faster the rate of release. For example, FIG. 6 illustrates the differences in release rate for two different forms (slab and microparticles). The ratio can be changed by altering the form factor of the hydrogel. Exemplary form factors include, but are not limited to, slabs, microflakes, microparticles, and powder. Methods of measuring the surface area of a material is known in the art, including the Brunauer Emmett Teller (BET) model. The ratio of surface area to volume can be in the range of about 1-150 $mm^{-1}$, e.g., about 2-100 $mm^{-1}$, about 5-100 $mm^{-1}$, or about 10-75 $mm^{-1}$.

When one of the eight parameters is predetermined, one can adjust at least one of the remaining seven parameters to achieve a desired release profile. For example, when the weight ratio of the biologic and excipient to the hydrogel is predetermined, one can adjust at least one of the following parameters: (a) the molar ratio of the nucleophilic group and the electrophilic group; (b) the number of the nucleophilic groups in the first precursor; (c) the number of the electrophilic groups in the second precursor; (d) the molecular weight of the first precursor; (e) the molecular weight of the second precursor; (f) a weight percentage of the biologic in a solid state formulation; and (g) a ratio of surface area to volume of the hydrogel.

In some embodiments, when two of the eight parameters are predetermined, one can adjust at least one of the remaining six parameters to achieve a desired release profile.

In some embodiments, when three of the eight parameters are predetermined, one can adjust the remaining five parameters to achieve a desired release profile.

In some embodiments, when four of the eight parameters are predetermined, one can adjust at least one of the remaining four parameters to achieve a desired release profile.

In some embodiments, when five of the eight parameters are predetermined, one can adjust at least one of the remaining three parameters to achieve a desired release profile.

In some embodiments, when six of the eight parameters are predetermined, one can adjust at least one of the remaining two parameters to achieve a desired release profile.

In some embodiments, when seven of the eight parameters are predetermined, one can adjust the remaining parameter to achieve a desired release profile.

A predictive model can be used for determining one or more of the parameters. In some embodiments, after one determines the desired release period and the molecular weights of the first and second precursors, the predictive model can provide the molar ratio that will result in the desired release period.

The desired release profile can depend on a variety of factors including, but not limited to, the biologic, the disease or condition being treated, and the administration route. In some embodiments, the desired release profile comprises a release period of about one week to six months for at least 90% biologic release, e.g., about two months to six months or about one week to two months. For ocular applications, the desired release profile can include controlled release for about 14 days. In some embodiments, the desired release profile exhibits near-linear release for about 1 week to 6 months. In some embodiments, the desired release profile exhibits near-linear release over at least one week. In some embodiments, the desired release profile exhibits near-linear release over at least two weeks. In some embodiments, the desired release profile exhibits near-linear release over at least one month. In some embodiments, the desired release profile exhibits near-linear release over at least two months. In some embodiments, the desired release profile exhibits near-linear release over at least six months.

A desired release profile can include a delayed-release portion, a sigmoidal shape, a linear portion, a non-linear portion, a logarithmic portion, an exponential portion, or a combination thereof. In some embodiments, a desired release profile may be a sigmoidal release profile with an extended delay with minimal or no release followed by a sustained release until depletion. Such a release profile might be desirable in combination with a liquid loading dose and tuned to begin the sustained release upon clearance of the initial loading dose to below effective levels from the body. Another desired release profile may be achieved through simultaneous administration of two or more hydrogels with tuned sigmoidal profiles to achieve a pulsatile release profile. Yet another desired release profile may be achieved through simultaneous administration of two or more hydrogels with different release profiles where one is fast (e.g., near linear release, logarithmic, or exponential) and another slower/delayed (sigmoidal).

Hydrogel Formation

In the presence of an anhydrous and hydrophobic solvent, the hydrogel can be formed by crosslinking the first precursor and the second precursor at the determined molar ratio around the solid state formulation having the biologic. In some embodiments, the anhydrous and hydrophobic solvent can be methylene chloride, ethyl acetate, dimethyl carbonate, chloroform, or a combination thereof.

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4,4' azobis(4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen-containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

A visualization agent may be used as a powder in a hydrogel; it reflects or emits light at a wavelength detectable to a human eye so that a user applying the hydrogel could observe the object when it contains an effective amount of the agent. Agents that require a machine aid for imaging are referred to as imaging agents herein, and examples include radioopaque contrast agents and ultrasound contrast agents.

Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the hydrogel, thus preserving visualization after application to a patient until the hydrogel hydrolyzes to dissolution.

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive visualization agents such as NHS-fluorescein can be used to incorporate the visualization agent into the molecular network of the hydrogel. The visualization agent may be present with either reactive precursor species, e.g., a crosslinker or functional polymer solution. The preferred colored substance may or may not become chemically bound to the hydrogel. The visualization agent may be used in small quantities, e.g., 1% weight/volume, more preferably less than 0.01% weight/volume and most preferably less than 0.001% weight/volume concentration; artisans will immediately appreciate that all the ranges and values within the explicitly stated ranges are contemplated. The agent tends to mark the location of the particle and provides an indication of its presence and dissolution rate.

The dehydrated hydrogel may be formed from the crosslinked hydrogel so that, upon hydration in physiological solution, a hydrogel is formed that is water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids.

For example, electrophilic groups such as N-hydroxysuccinimidyl glutarate, N-hydroxysuccinimidyl succinate, N-hydroxysuccinimidyl carbonate, N-hydroxysuccinimidyl adipate or N-hydroxysuccinimidyl azelate may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

A biodegradable linkage in the hydrogel and/or precursor may be water-degradable or enzymatically degradable. Illustrative water-degradable biodegradable linkages include polymers, copolymers and oligomers of glycolide, dl-lactide, 1-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Matrix materials may be chosen so that degradation products are absorbed into the circulatory system and essentially cleared from the body via renal filtration. The matrix materials may be hydrogels in a physiological solution. One method is to choose precursors that are not broken down in the body, with linkages between the precursors being degraded to return the precursors or precursors with small changes caused by the covalent crosslinking process. This approach is in contrast to choosing biological matrix materials that are destroyed by enzymatic processes and/or materials cleared by macrophages, or that result in by-products that are effectively not water soluble. Materials that are cleared from the body by renal filtration can be labeled and detected in the urine using techniques known to artisans. While there might be at least a theoretical loss of some of these materials to other bodily systems, the normal fate of the material is a kidney clearance process. The term "essentially cleared" thus refers to materials that are normally cleared through the kidneys.

Applications

In some embodiments, a hydrogel material may be placed into the patient, e.g., in a tissue or organ, including intraocularly, intravitreally, superchoroidally, subconjunctivally, topically, subcutaneously, intramuscularly, intraperitoneally, in a potential space of a body, or in a natural cavity or opening. The material provides a depot for release of a therapeutic agent (e.g., a biologic) over time. Embodiments thus include between about 0.05 and about 500 ml volumes for placement (referring to total volume in the case of particle collections delivered); artisans will immediately appreciate that all the ranges and values within the explicitly stated ranges are contemplated, e.g., from 1 to 10 ml or from 5 to 50 ml. Intraperitoneal or intramuscular injection, for instance, is a useful area for extended control release of agents over hours, days, or weeks.

The materials described herein may be used to deliver drugs or other therapeutic agents (e.g., imaging agents or markers). One mode of application is to apply a mixture of hydrogel particles and other materials (e.g., therapeutic agent, buffer, accelerator, initiator) through a needle, cannula, catheter, or hollow wire to a site. The mixture may be delivered, for instance, using a manually controlled syringe or mechanically controlled syringe, e.g., a syringe pump. Alternatively, a dual syringe or multiple-barreled syringe or multi-lumen system may be used to mix the hydrogel particles at or near the site with a hydrating fluid and/or other agents.

The dehydrated hydrogels may be provided in flowable form to the site, e.g., as flowable particles. The hydrogels may be suspended in a liquid and applied to the site. The hydrogel particles may be made to have a maximum diameter for manual passage out of a syringe through a 3 to 5 French catheter, or a 10 to 30 gauge needle. Artisans will immediately appreciate that all the ranges and values within the explicitly stated ranges are contemplated, e.g., 25 to 30 gauge. The use of small needles is particularly advantageous in the eye, which is a sensitive organ. Applications to other organs are also advantageous, e.g., to control bleeding or other damage. The particles may be formed by creating a hydrogel and then breaking it up into smaller pieces. The hydrogel may be, e.g., ground in a ball mill or with a mortar and pestle, or chopped or diced with knives or wires. Or the hydrogel may be cut up in a blender or similar apparatus. The hydrogel may also be forced through a mesh or casted into a template mold with desired size and shape. The hydrogel may contain the therapeutic agent-loaded particles. Some or all of the hydrogel particles may contain the therapeutic agent-loaded particles. In some embodiments, a first set of therapeutic agent-loaded particles loaded with a first therapeutic agent is included inside a first set of hydrogel particles and a second set of therapeutic agent-loaded particles loaded with a second therapeutic agent is included inside a second set of hydrogel particles. In this manner, a plurality of therapeutic agents may be released from a single implant. Embodiments of the particles include those with a particular shape such as sphere, rod, or disc.

Embodiments include placement of a plurality of hydrogel particles. The hydrogel particles may comprise a therapeutic agent. The particles may be made with a size for manual passage through a 25-gauge or smaller diameter needle. The pressure to force the particles through the needle may be provided manually.

An alternative to delivery of particles is to pre-form the gel as a shaped article and then introduce the material into the body. For example, the hydrogels may be formed as spheres, rods, cylinders, or other shapes. Embodiments include solid rods of hydrogels for subcutaneous implantation and delivery of one or more therapeutic agents.

Hydrogels as set forth herein may be used for tissue augmentation. The use of collagen for dermal augmentation is well known. Hydrogels, for example, may be used for dermal filler or for tissue augmentation. Embodiments include injecting or otherwise placing a plurality of particles in a tissue, or forming a hydrogel in situ. The material may be injected or otherwise placed at the intended site.

Hydrogels as set forth herein may be used to separate tissues to reduce a dose of radioactivity received by one of the tissues. As set forth in U.S. Pat. No. 7,744,913, which is hereby incorporated by reference herein for all purposes with the present specification controlling in case of conflict, spacer materials may be placed in a patient. Certain embodiments are a method comprising introducing a spacer to a position between a first tissue location and a second tissue location to increase a distance between the first tissue location and the second tissue location. Further, there may be a step of administering a dose of radioactivity to at least the first tissue location or the second tissue location. A method, for example, is delivering a therapeutic dose of radiation to a patient comprising introducing a biocompatible, biodegradable particulate hydrogel, e.g., a collection of particles optionally with radioopaque contents, between a first tissue location and a second tissue location to increase a distance between the first tissue location and the second tissue location, and treating the second tissue location with the therapeutic dose of radiation so that the presence of the filler device causes the first tissue location to receive less of the dose of radioactivity compared to the amount of the dose of radioactivity the first tissue location would receive in the absence of the spacer. The spacer may be introduced as a dehydrated hydrogel that forms a hydrogel in the patient that is removed by biodegradation of the spacer-hydrogel in the patient. An example is the case wherein the first tissue location is associated with the rectum and the second tissue location is associated with the prostate gland. The amount of reduction in radiation can vary. Embodiments include at least about 10% to about 90%; artisans will immediately appreciate that all the ranges and values within the explicitly stated ranges are contemplated, e.g., at least about 50%. The radiation may alternatively be directed to a third tissue so that the first tissue or the second tissue received a lower amount of radiation as a result of its separation from the other tissue(s). The first tissue and the second tissue may be adjacent to each other in the body, or may be separated from each other by other tissues. Spacer volumes for separating tissues are dependent on the configuration of the tissues to be treated and the tissues to be separated from each other. In many cases, a volume of about 20 cubic centimeters (cc's or mls) is suitable. In other embodiments, as little as about 1 cc might be needed. Other volumes are in the range of about 5-1000 cc; artisans will immediately appreciate that all the ranges and values within the explicitly stated ranges are contemplated, e.g., 10-30 cc. In some embodiments, spacers are administered in two doses at different times so as to allow the tissues to stretch and accommodate the spacer and thereby receive a larger volume of spacer than would otherwise be readily possible. Tissues to be separated by a spacer include, for example, at least one of a rectum, prostate, and breast, or a portion thereof. For instance, a first portion of a breast may be separated from a second portion.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

All definitions, as defined and used herein, should be understood to control over dictionary definitions, definitions in documents incorporated by reference, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the terms "release profile" and "release kinetics" are used interchangeably to refer to the manner a biologic is released from the hydrogel under physiological conditions as a function of time. A release profile can be characterized by a release period and one or more release rates during the release period. A release profile can be visualized by a graph having time on the X-axis and a measure of biologic release on the Y-axis (e.g. percentage, cumulative mass of released biologic, or ratio of cumulative mass of released biologic to total hydrogel mass).

As used herein, the term "near-linear release" refers to a release rate proportional to $t^n$, where t is time, and n is in the range of 0.5-1. Artisans will immediately appreciate that all the ranges and values within the explicitly stated ranges are contemplated, e.g., 0.5 to 0.95, 0.5 to 0.9, 0.5 to 0.85, 0.5 to 0.8, 0.6 to 0.95, 0.6 to 0.9, 0.6 to 0.85, 0.6 to 0.8, 0.7 to 0.95, 0.7 to 0.9, 0.7 to 0.85, or 0.7 to 0.8. In some embodiments, n is 0.5. In some embodiments, n is 0.55. In some embodiments, n is 0.6. In some embodiments, n is 0.65. In some embodiments, n is 0.7. In some embodiments, n is 0.75. In some embodiments, n is 0.8. In some embodiments, n is 0.85. In some embodiments, n is 0.9. In some embodiments, n is 0.95. In some embodiments, n is 1.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Described herein are illustrative examples of how these parameters independently, as well as in combination, impact release kinetics and how they can be leveraged to meet specific target product profiles. mAb IgG1 and mAb IgG4 are used as model monoclonal antibodies for the majority of results presented in this report with a data set also including mAb bispecific and Trap protein. In general, the results presented here could be extended to other monoclonal antibodies (mAbs) or proteins similar in size to the mAbs used here.

The protein hydrogel delivery system is fabricated by reacting two branched PEG reagents with complimentary reactive end-groups in the presence of spray dried protein suspended in an organic solvent. Upon reacting, the PEG reagents form a cross-linked network entrapping the spray dried protein, which remains in the solid state. The solvent is then removed from the resulting mAb loaded polymer matrix, leaving behind a solid dehydrated mAb hydrogel drug product, termed mAb-XPEG. The organic solvent is chosen for compatibility with the spray dried protein, which needs to be insoluble in the solvent and stable, and for processing considerations. In all experiments presented here, dichloromethane (DCM) was used as the reaction solvent and was chosen for its compatibility with the selected proteins as well as volatility, allowing for easy drying of the mAb-XPEG matrix at room temperature under vacuum. The mAb-XPEG matrix can be formed as a slab or cast as a film or into a mold; after drying, the solid matrix can be further cut into shapes and/or particles with specific geometries.

When the mAb-XPEG drug product is hydrated, the matrix, being a hydrogel, swells. Upon hydration, a portion of the loaded spray dried mAb will dissolve and diffuse from the matrix. In this initial phase, protein release from the matrix is diffusion based and exhibits a dependence on the square root of time. The remainder of the protein, being exposed to high concentrations of PEG in the local microenvironments within the polymer matrix, will remain in the solid state until hydrogel dissolution progresses to the point at which the PEG concentration in the local microenvironment drops to a level allowing for protein dissolution. Thus, with passing time in the hydrated environment, the cross-linking in the PEG matrix degrades due to hydrolysis, resulting in protein dissolution and subsequent diffusion from the polymer matrix. In this phase of release, matrix dissolution is the rate-limiting step, and protein release is exponential as a function of time. Finally, when the matrix has degraded to a point at which no solid protein remains, release of the remaining protein in solution within the matrix is once again controlled by diffusion through the remaining matrix. These phases of protein release from the matrix give rise to the characteristic sigmoidal shape of the release profile (FIG. 1).

In Phase I of FIG. 1, upon hydration, a portion of loaded protein exposed to surface or in regions of low PEG density is solubilized. Protein particles on or near surface are immediately released as "burst" release. This is evidenced by an increase in burst release correlating with an increase in surface area to volume (mass). Protein dissolved upon hydration, presumably in regions with low PEG density, but not at surface, is available for release in the "diffusion" phase. This is evidenced by an increase in the amount of protein released during the diffusion phase with increasing molar ratio of NH:NHS. Without wishing to be bound by theory, by increasing molar ratio, fewer cross-links are formed and regions with PEG density low enough to allow for dissolution of protein particles will be more prevalent. In this phase, diffusion follows Fickian diffusion with the driving force of diffusion being the concentration of solubilized protein, but is slowed by the porous network created by PEG cross-linking, and thus the rate of release during this diffusion phase may be impacted by the extent and structure of the PEG cross-linking.

In Phase II of FIG. 1, the dissolution phase starts when the cleavage of PEG cross-linking reaches an extent at which it becomes the rate-limiting step for protein release from the matrix. Without wishing to be bound by theory, cleavage of PEG cross-linking is a first order process, and as it occurs it is expected to both decrease PEG density within the matrix, allowing for the solubilization of protein particles, as well as increase the rate of diffusion of protein through the PEG matrix as the porous network opens up. The point in the release profile in which dissolution-controlled release is observed takes place when the overall rate of diffusion of protein from the matrix is faster than the effective dissolution of the cross-linking. The shape of the release profile during the dissolution phase is a direct correlation to the first order process of dissolution. The rate of release and duration of the dissolution phase is expected to depend on the extent of cross-linking (molar ratio of NH:NHS), the rate of cleavage, and the total amount of protein remaining in the matrix upon initiation of this phase.

In Phase III of FIG. 1, the depletion phase occurs when once again Fickian diffusion is rate limiting. In this phase, all protein has presumably been dissolved within the matrix and the driving force of diffusion for release is decreasing as the remaining protein depletes from the matrix. This is evidenced by the characteristic shape (linear with respect to square root of time) of the release profiles just prior to the plateau indicating depletion. Depending on protein load and the kinetics and duration of release during the diffusion and dissolution phase, this phase may occur well before full gel dissolution.

Table 1 lists the formulation parameters theoretically associated with release kinetics in the protein loaded hydrogel drug delivery system. These parameters have been separated into three categories: factors based on the selection of polymer reagents, factors relating to the spray dried protein formulation, and factors determined in the mAb-XPEG fabrication. This list only considers formulation related parameters and does not include process parameters such as solvent, reagent concentrations, reaction conditions, etc. For all studies included here, such process parameters are kept constant.

TABLE 1 mAb-XPEG Formulation Parameters

| Polymer Reagents (PEGNH & PEGNHS) | Spray Dried Protein Formulation | Hydrogel Fabrication & Form |
|---|---|---|
| Branching (4-arm/8-arm) Molecular Weight End Group (controls rate of crosslinking hydrolysis) | Protein content Particle Size/Distribution Molecule Powder Properties | Extent of cross-linking ("molar ratio NH:NHS") Solid Loading Surface Area:Volume Ratio (form factor) |

The rationale behind focusing efforts on leveraging the protein-loaded hydrogel fabrication and spray-dried protein formulation and limiting the choice of polymer reagents (i.e., MW and same functional end group chemical structure) is to simplify, from a CMC (chemistry, manufacturing, and control) and regulatory perspective, the complexity of the platform by limiting the number of PEG reagents to two. However, it should be noted that similar tuning can be achieved in this system by leveraging different polymer characteristics (e.g., functional end group chemical structure) to impact diffusion of protein within the matrix and dissolution rate of the hydrogel matrix.

Considering the spray-dried formulation parameters in understanding release kinetics is a key factor for platform development of this delivery system. While the spray-dried formulation may be leveraged to achieve desired release kinetics, the formulation may also be dictated based on protein stability. While molecules may behave similarly when loaded into the hydrogel matrix in regards to release kinetics, protein stability is known to be molecule specific and different proteins may require changes to the spray-dried formulation to maintain stability either in the manufacturing process or during storage as intermediate drug substance or protein loaded hydrogels. It is therefore important, in either case, to understand how spray-dried formulations will impact release kinetics. This is similarly true for the surface area to volume ratio as a hydrogel fabrication parameter. While in some instances surface area to volume may be leveraged to achieve desired release kinetics, it may also be dictated or limited by the form factor required for administration (e.g., to be syringeable or as an implant).

Materials and Methods

TABLE 2

Spray-Dried Protein Formulations, Reagents, and Materials Used in protein-loaded hydrogel Fabrication and in vitro release (IVR) Studies

| | Material | Protein content in Spray-Dried Powder |
|---|---|---|
| Spray Dried Protein Formulations | mAb IgG1 | 80% w/w |
| | mAb IgG1 | 90% w/w |
| | mAb IgG1 | 50% w/w |
| | mAb IgG4 | 40% w/w |
| | mAb IgG4 | 80% w/w |
| | mAb IgG4 | 90% w/w |
| | mAb IgG4 | 50% w/w |
| | mAb bispecific | 80% w/w |
| | Trap Protein | 70% w/w |
| PEG Reagents | PEG-NH | 8-arm NH-PEG, 14450 Da MW [Hexaglycerol octa(aminopropyl)polyoxyethylene] |
| | PEG-NHS | 8-arm NHS-PEG, glutaryl, 45573 Da MW [Hexaglycerol octa(succinimidyloxyglutaryl)polyoxyethylene] |
| Reaction Solvent | DCM | Dichloromethane |
| IVR Media | PBS, pH 7.4 | 4 mM PO4, 155 mM NaCl, 0.03% PS20, pH 7.4 |

TABLE 3 mAb-XPEG Design Space Multifactorial Study I

| Factor | Range Tested |
|---|---|
| Molar ratio | 0.9-1.8 NH:NHS |
| Solid Loading | 0.6-0.9 w/w |
| Protein Content | 0.4-0.8 w/w |
| Molecule | mAb IgG1, mAb IgG4 |

In Table 3, ranges and factors included in multifactorial analysis of impact of protein-loaded hydrogel formulation parameters on protein release kinetics. Surface area to volume is not controlled in this evaluation. Samples are specified in Table 4.

TABLE 4

Protein-loaded hydrogel Design Space Multifactorial Study I.

| Sample ID | Molecule | Total Solid Loading (w/w) | Spray-Dried Protein Content (w/w) | Actual molar ratio (NH:NHS) |
|---|---|---|---|---|
| MAB2RS001F1 | mAb IgG4 | 0.9 | 0.4 | 1.2 |
| MAB2RS001F2 | mAb IgG4 | 0.9 | 0.4 | 1.2 |
| MAB2RS003F1 | mAb IgG4 | 0.9 | 0.4 | 1.5 |
| MAB2RS005F5 | mAb IgG4 | 0.9 | 0.8 | 1.4 |
| MAB2RS005F6 | mAb IgG4 | 0.9 | 0.8 | 1.6 |
| MAB2RS006F4 | mAb IgG4 | 0.8 | 0.8 | 0.8 |
| MAB2RS006F5 | mAb IgG4 | 0.9 | 0.8 | 1.4 |
| MAB2RS006F6 | mAb IgG4 | 0.9 | 0.8 | 1.6 |
| MAB1RS004F1B | mAb IgG1 | 0.6 | 0.8 | 1.2 |
| MAB1RS004F1C | mAb IgG1 | 0.6 | 0.8 | 1.2 |
| MAB1RS017F1A | mAb IgG1 | 0.6 | 0.8 | 1.1 |
| MAB1RS017F1B | mAb IgG1 | 0.6 | 0.8 | 1.3 |
| MAB1RS017F1C | mAb IgG1 | 0.7 | 0.8 | 1.8 |
| MAB1RS017F2A | mAb IgG1 | 0.7 | 0.8 | 1.0 |
| MAB1RS017F2B | mAb IgG1 | 0.7 | 0.8 | 1.0 |
| MAB1RS017F2C | mAb IgG1 | 0.7 | 0.8 | 1.0 |
| MAB1RS017F3A | mAb IgG1 | 0.8 | 0.8 | 1.0 |
| MAB1RS017F3B | mAb IgG1 | 0.9 | 0.8 | 1.5 |

TABLE 5

Protein-loaded hydrogel Design Space Multifactorial Study II.

| Factor | Range Tested |
|---|---|
| Molar ratio | 1.1-2.0 NH:NHS |
| Solid Loading | 0.2-0.7 w/w |
| Protein Content | 0.5-0.9 w/w |
| Molecule | mAb IgG1, mAb IgG4 |
| Surface Area to Volume Ratio | 3-79 (mm$^{-1}$) |

In Table 5, ranges and factors included in multifactorial analysis of impact of protein-loaded hydrogel formulation parameters on mAb release kinetics. Ranges expanded from Study I and Surface Area:Volume Ratio included as Factor. Samples are specified in Table 6.

TABLE 6

Protein-loaded hydrogel Design Space Multifactorial Study II.

| SampleID | Molecule | Spray-Dried Protein Content (w/w) | Actual molar ratio (NH:NHS) | Total Solid Loading (w/w) | S:V mm$^{-1}$ | S:V Category |
|---|---|---|---|---|---|---|
| mAb2A | mAb IgG4 | 0.5 | 1.1 | 0.7 | 35 | High |
| mAb2B | mAb IgG4 | 0.9 | 2.0 | 0.7 | 24 | High |
| mAb2C | mAb IgG4 | 0.5 | 1.5 | 0.2 | 79 | High |
| mAb2D | mAb IgG4 | 0.9 | 1.8 | 0.7 | 6 | Medium |
| mAb2F | mAb IgG4 | 0.5 | 2.0 | 0.2 | 3 | Low |
| mAb2G | mAb IgG4 | 0.5 | 1.1 | 0.7 | 3 | Low |
| mAb2D2 | mAb IgG4 | 0.9 | 1.8 | 0.7 | 4 | Low |
| mAb2E | mAb IgG4 | 0.9 | 1.2 | 0.2 | 4 | Low |
| mAb1-A | mAb IgG1 | 0.9 | 1.2 | 0.2 | 53 | High |
| mAb1-B | mAb IgG1 | 0.5 | 1.1 | 0.7 | 4 | Medium |
| mAb1-C | mAb IgG1 | 0.5 | 2.0 | 0.2 | 4 | Medium |
| mAb1-D | mAb IgG1 | 0.9 | 1.5 | 0.7 | 4 | Medium |
| mAb1-E | mAb IgG1 | 0.5 | 1.5 | 0.7 | 35 | High |
| mAb1-F | mAb IgG1 | 0.5 | 2.0 | 0.2 | 52 | High |
| mAb1-G | mAb IgG1 | 0.9 | 1.9 | 0.7 | 3 | Low |
| mAb1-H | mAb IgG1 | 0.9 | 1.2 | 0.2 | 3 | Low |

The mAb-XPEG fabrication protocol is shown below.

I. Reagent Preparation:
Add PEG reagents into separate tubes.
Add DCM.
Mix thoroughly until PEG reagents are dissolved.
Add PEG-NH solution to each vial of spray-dried protein.
Swirl and sonicate to suspend protein in PEG-NH solution. And
Record weight after every step.
II. Crosslinking Reaction:
Add PEG-NH/Protein suspension and mix while dispensing.
The molar ratio (NH:NHS) is determined based on the weight of PEG-NHS solution and PEG-NH/Protein suspension added during fabrication assuming homogeneous solutions/suspensions.
Leave at room temperature in vacuum chamber or fume hood, uncapped, overnight to allow for solvent evaporation.

Conclusions

FIGS. 2-6 show examples of the impact of independent factors on release profiles.

Figure 7:
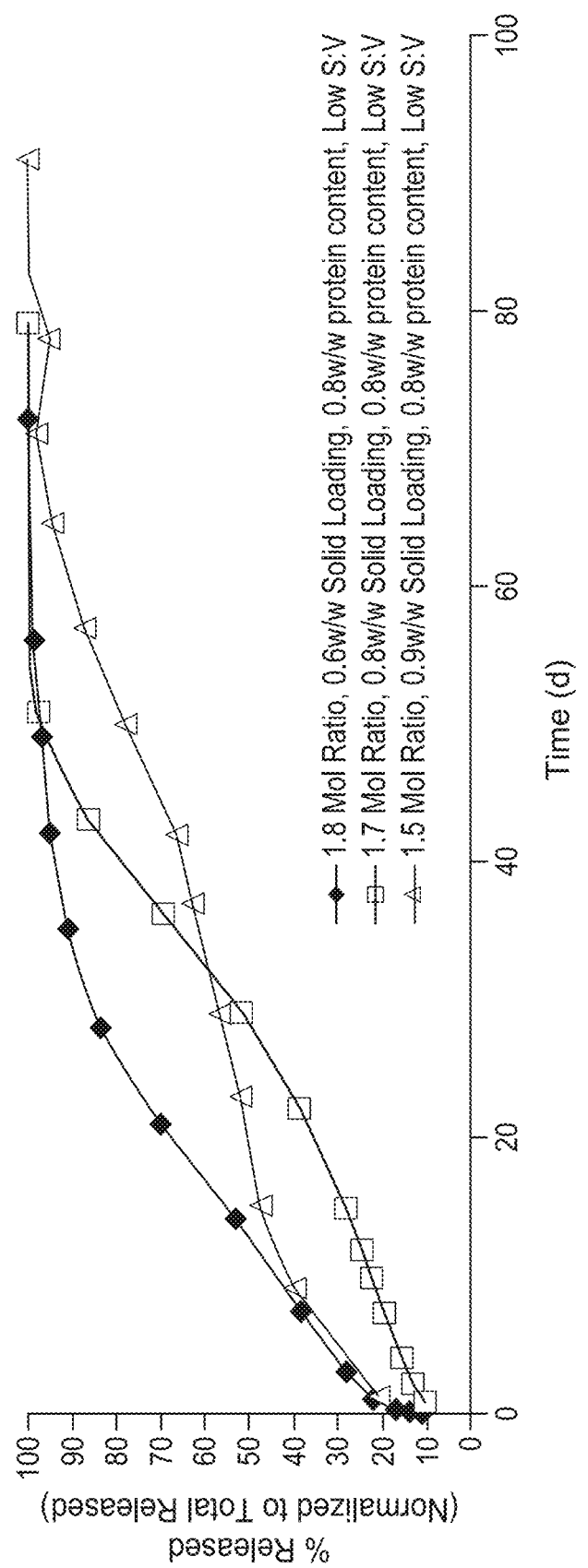
FIG. 7 is a graph showing how multiple factors can be adjusted together to tune release profiles to achieve near linear release for 1-3 months. All protein loaded hydrogels shown in this figure contain 40 kDa PEG-NHS HGEO and 15 kDa PEG-NH HGEO PEG components, mAb IgG1, 82% protein content in slab form with 1.8 molar ratio and 60% solid loading (diamonds), 1.7 molar ratio and 80% solid loading (squares), or 1.5 molar ratio and 90% solid loading (triangles).
Figure 8:
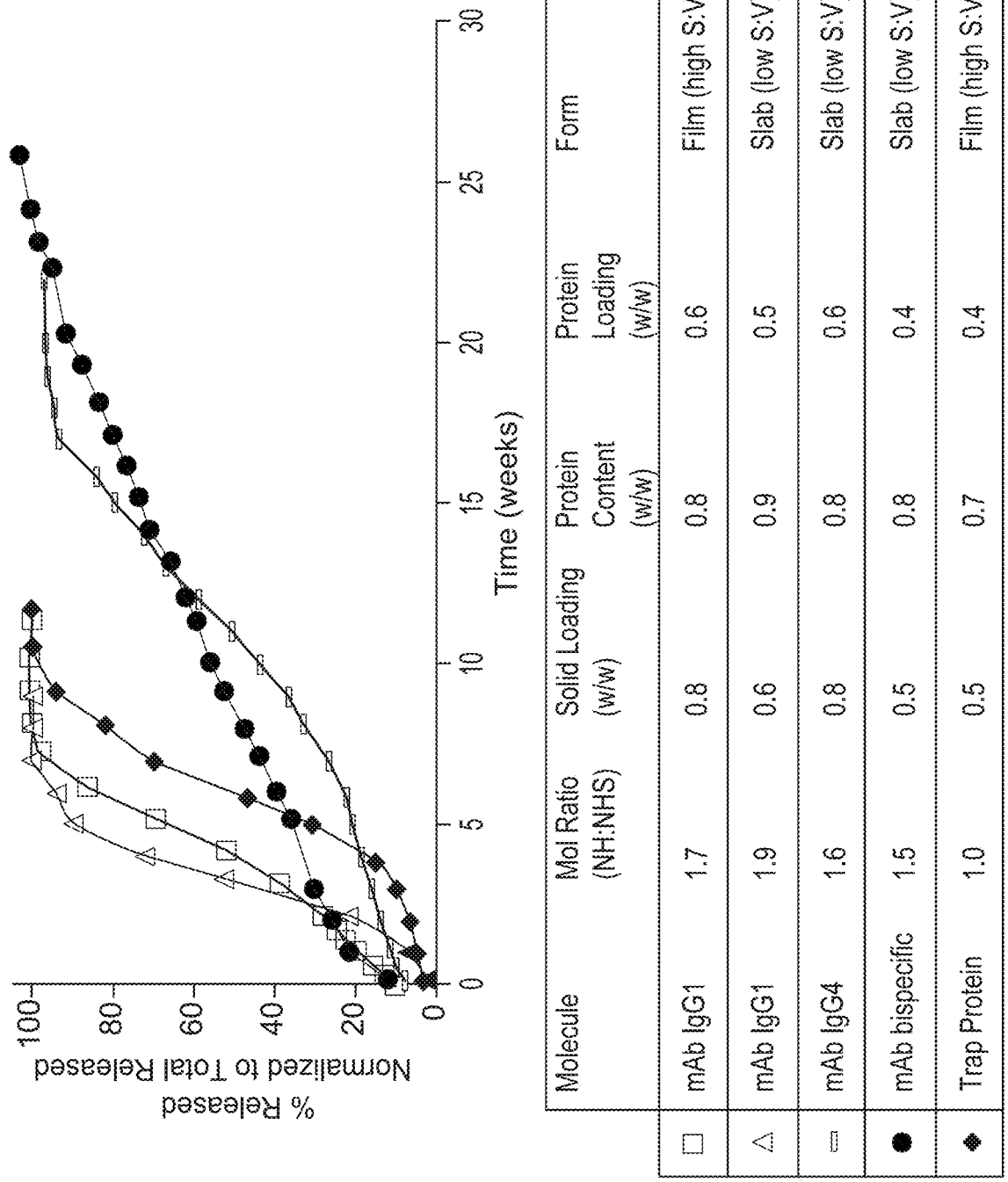
FIG. 8 is a graph showing near linear release for five different protein loaded hydrogel formulations with four different mAbs and one Trap protein (i.e., a fusion protein with decoy receptor domains). All protein-loaded hydrogel formulations shown in this figure contain 40 kDa PEG-NHS HGEO and 15 kDa PEG-NH HGEO PEG components.

FIGS. 7-8 shows examples of leveraging important formulation parameters to tune release profiles.

Figure 9:
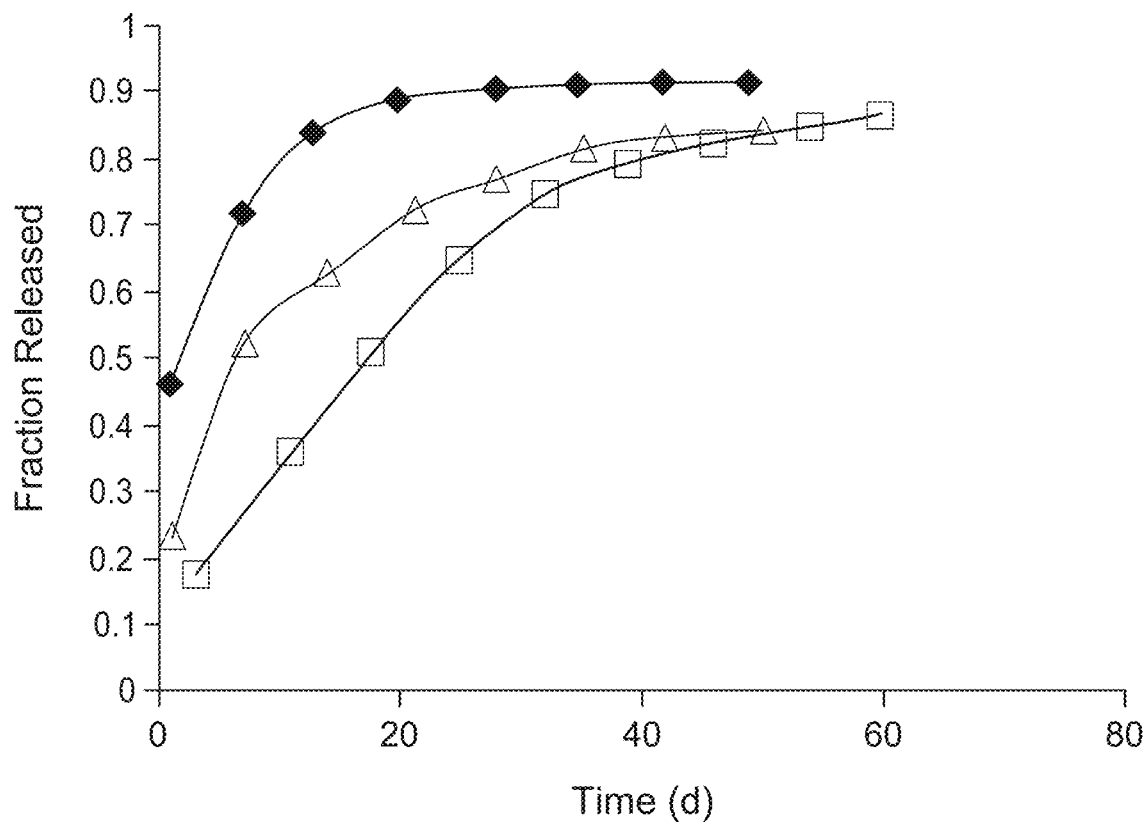
FIG. 9 is a graph showing how, in microparticle format with high surface area to volume ratio, release profiles can be tuned to be more linear with longer duration through adjusting a combination of factors including molar ratio, protein content, and solid loading. All protein loaded hydrogel formulations shown in this figure contain 40 kDa PEG-NHS HGEO and 15 kDa PEG-NH HGEO PEG components and mAb IgG1 and are produced as microparticles.
Figure 11:
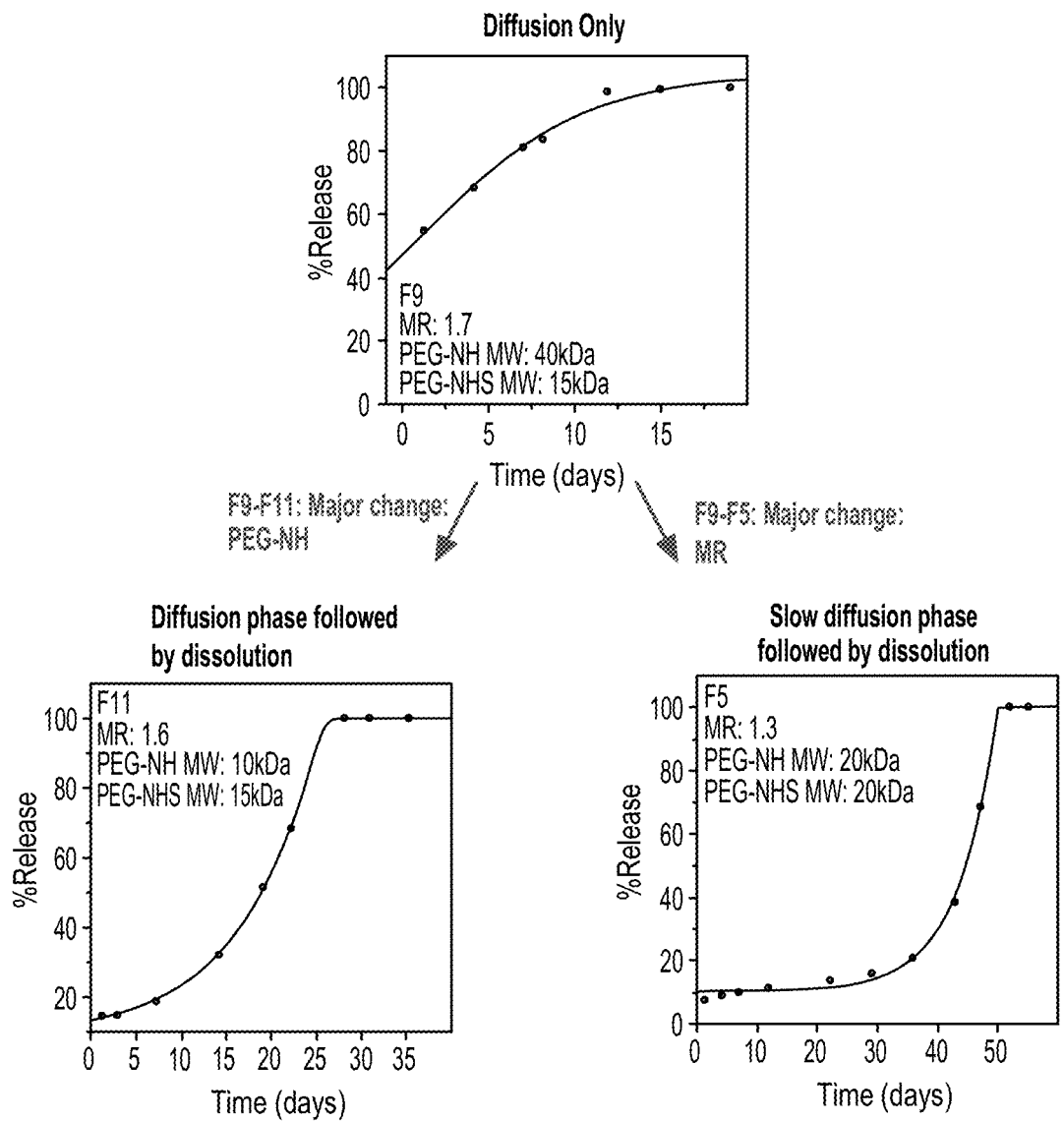
FIG. 11 shows that release is driven by three main mechanisms: diffusion, dissolution, and depletion. Initial release (burst) will be largely driven by hydration of the gel and diffusion of protein from the outer portion of the matrix; diffusion will be limited by crosslinking that prevents hydration of encapsulated protein within the matrix. For dissolution, once crosslinks are hydrolyzed by aqueous media, additional protein will become exposed, hydrated, and released from the matrix until the drug load is depleted. Release kinetics can be tuned to the target duration and desired shape by adjusting combinations of PEG MW and molar ratio.
Figure 12:
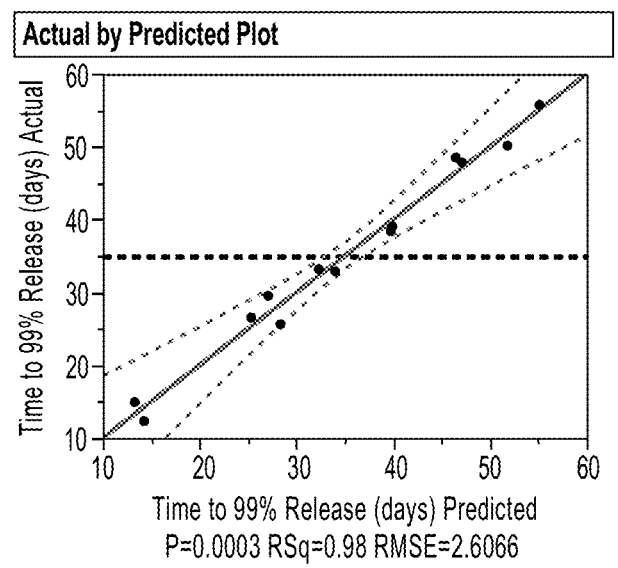
FIG. 12 shows that Actual by Predicted scatter plot of the measured time to 99% release vs. the predicted time to 99% release based on model parameters. The goodness-of-fit for the predictive model for 99% release is indicated by RSquare Adj (>96%).
Figure 13:
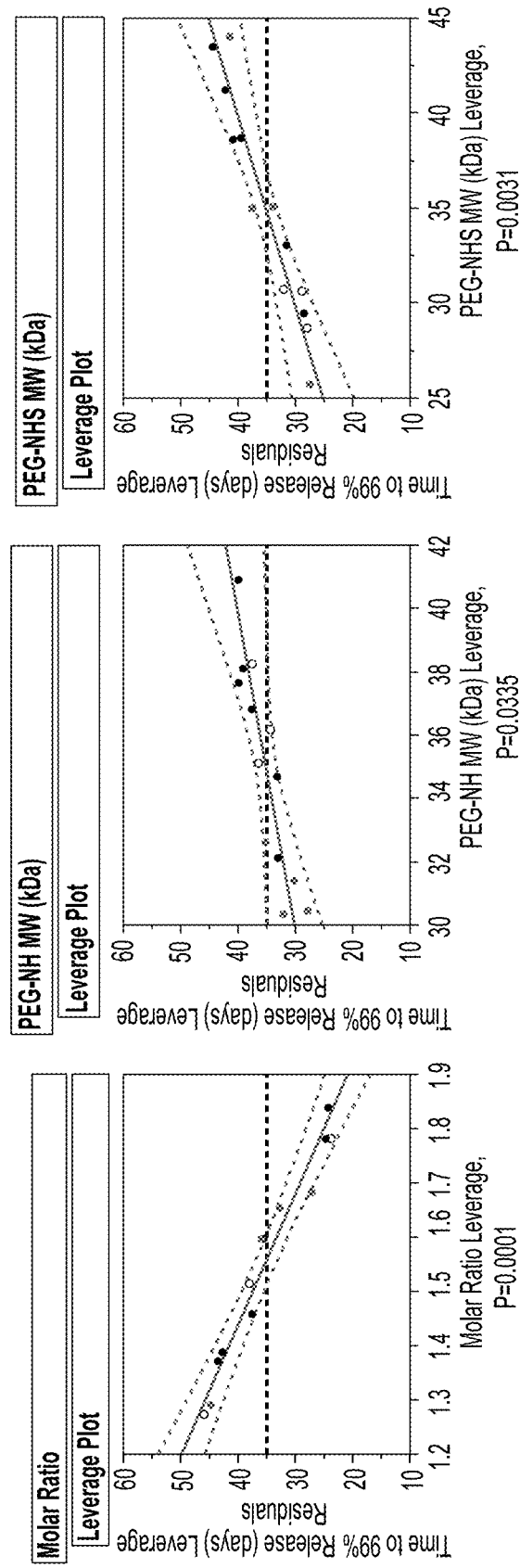
FIG. 13 shows that all three main factors have a statistically significant impact (p<0.05) on time to total release (99%). Magnitude of each effect in rank order is: 1. Molar Ratio (continuous factor-negative correlation); 2. PEG-NHS molecular weight (categorical factor, i.e., non-continuous or discrete); and 3. PEG-NH molecular weight (categorical factor). 40 kDa PEG-NH (highlighted in gray circles) has the largest effect of PEG-NH reagents tested. 15 kDa PEG-NHS (highlighted in open circles) has the largest effect of PEG-NHS reagents tested.
Figure 14:
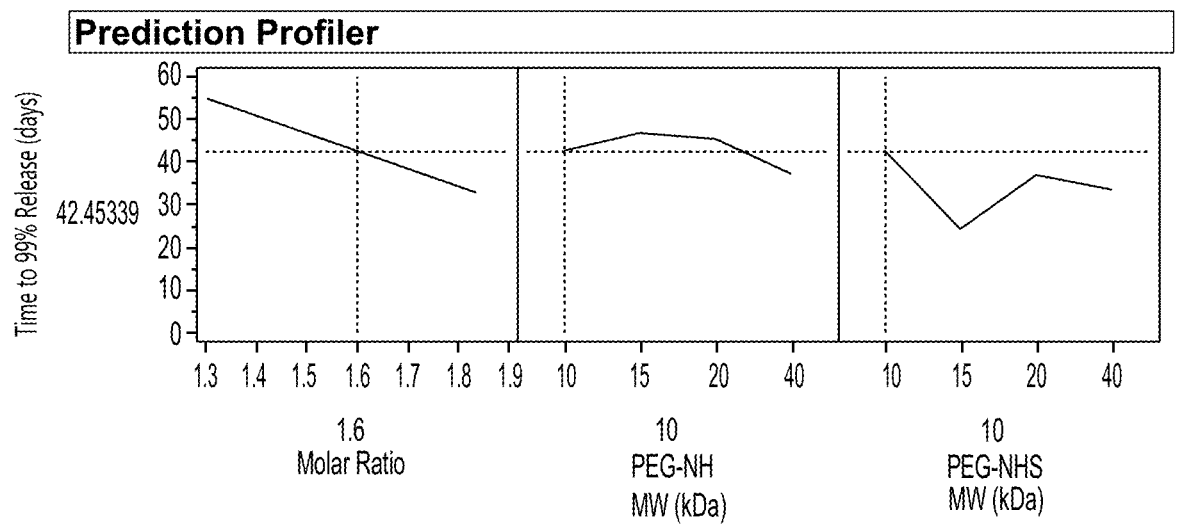
FIG. 14 is a graph showing that, in accordance with the predictive model, a combination of a molar ratio of 1.6, PEG-NH molecular weight (MW) of 10 kDa, and PEG-NHS MW of 10 kDa can produce a hydrogel with a release period of 42.5 days for 99% release.
Figure 15:
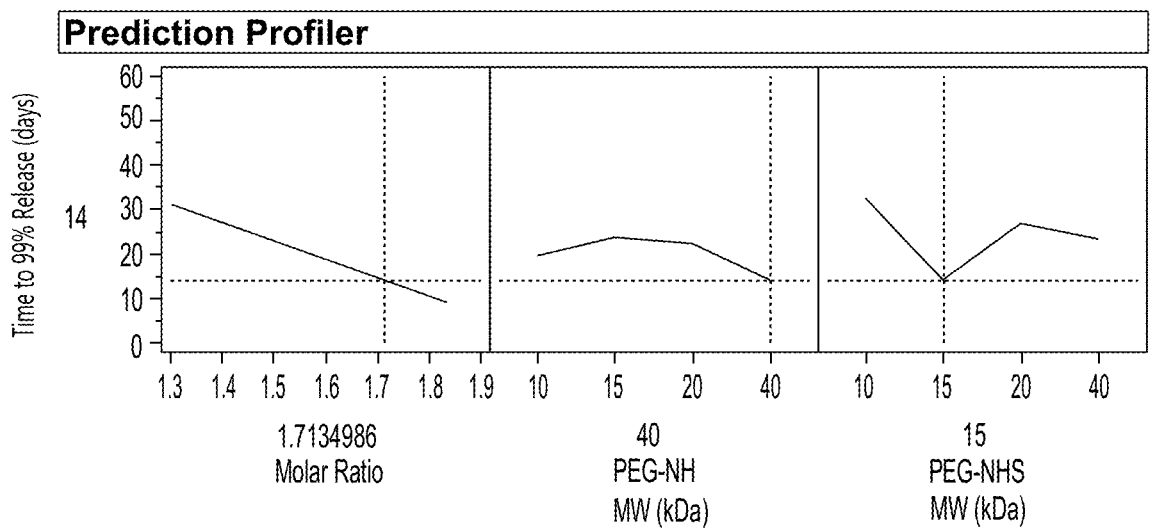
FIG. 15 is a graph showing that, in accordance with the predictive model, a combination of a molar ratio of 1.71, PEG-NH MW of 40 kDa, and PEG-NHS MW of 15 kDa can produce a hydrogel with a release period of 14 days for 99% release.
Figure 16:
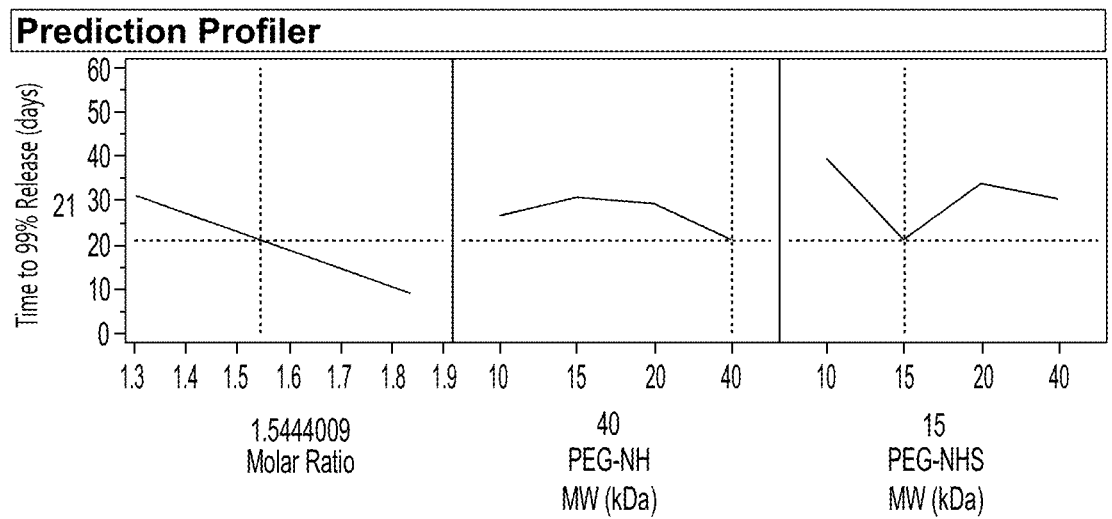
FIG. 16 is a graph showing that, in accordance with the predictive model, a combination of a molar ratio of 1.54, PEG-NH MW of 40 kDa, and PEG-NHS MW of 15 kDa can produce a hydrogel with a release period of 21 days for 99% release.
Figure 17:
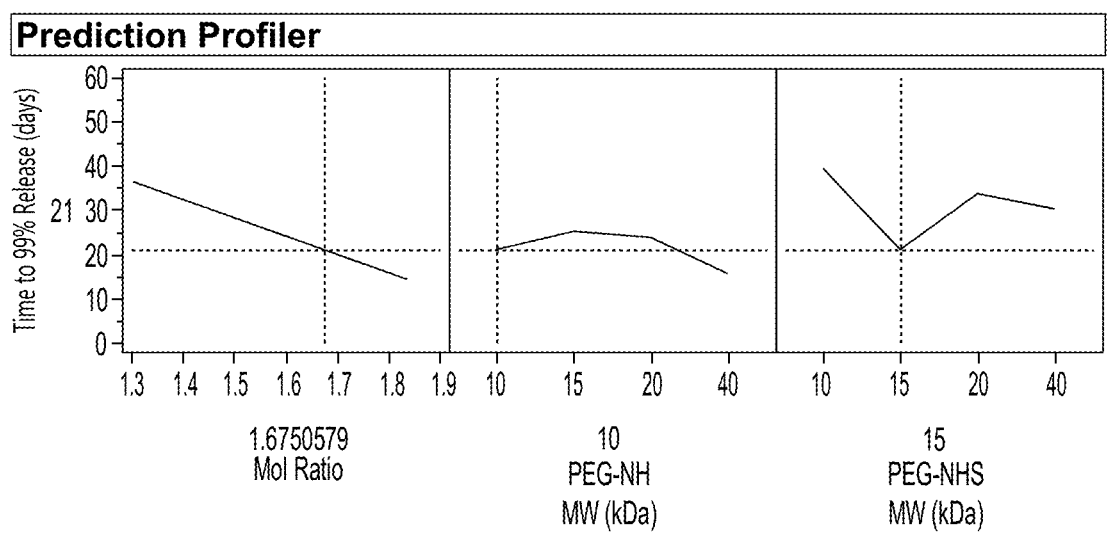
FIG. 17 is a graph showing that, in accordance with the predictive model, a combination of a molar ratio of 1.68, PEG-NH MW of 10 kDa, and PEG-NHS MW of 15 kDa can produce a hydrogel with a release period of 21 days for 99% release.
Figure 18:
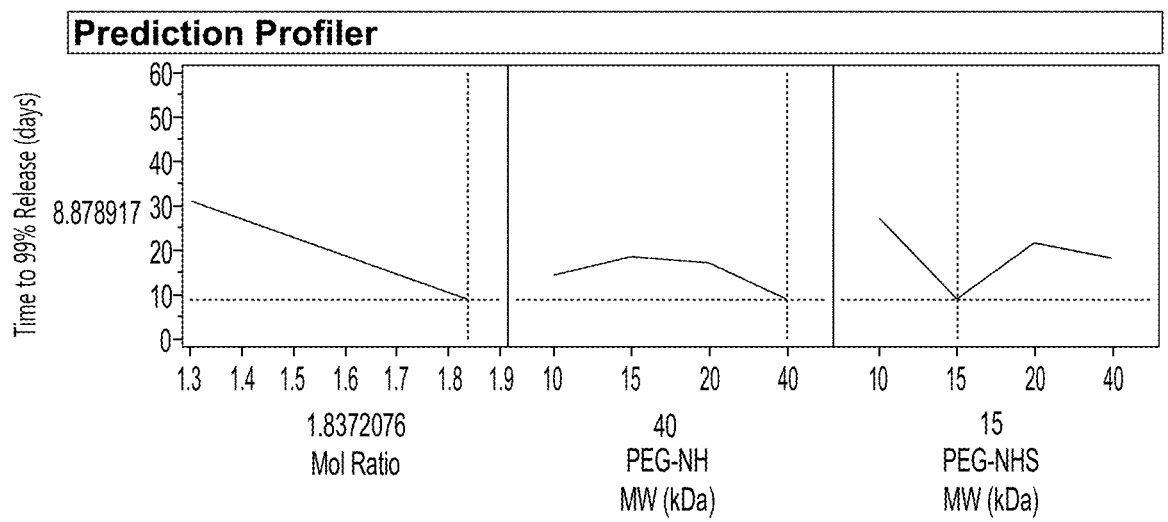
FIG. 18 is a graph showing that, in accordance with the predictive model, a combination of a molar ratio of 1.84, PEG-NH MW of 40 kDa, and PEG-NHS MW of 15 kDa can produce a hydrogel with a release period of 8.88 days for 99% release.
Figure 19:
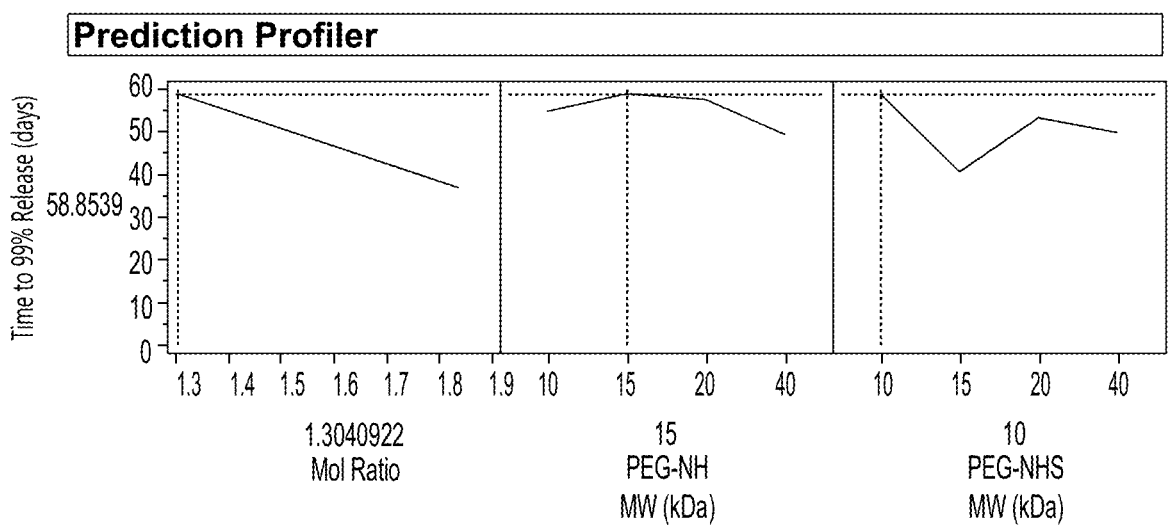
FIG. 19 is a graph showing that, in accordance with the predictive model, a combination of a molar ratio of 1.30, PEG-NH MW of 15 kDa, and PEG-NHS MW of 10 kDa can produce a hydrogel with a release period of 58.9 days for 99% release.
Figure 20:
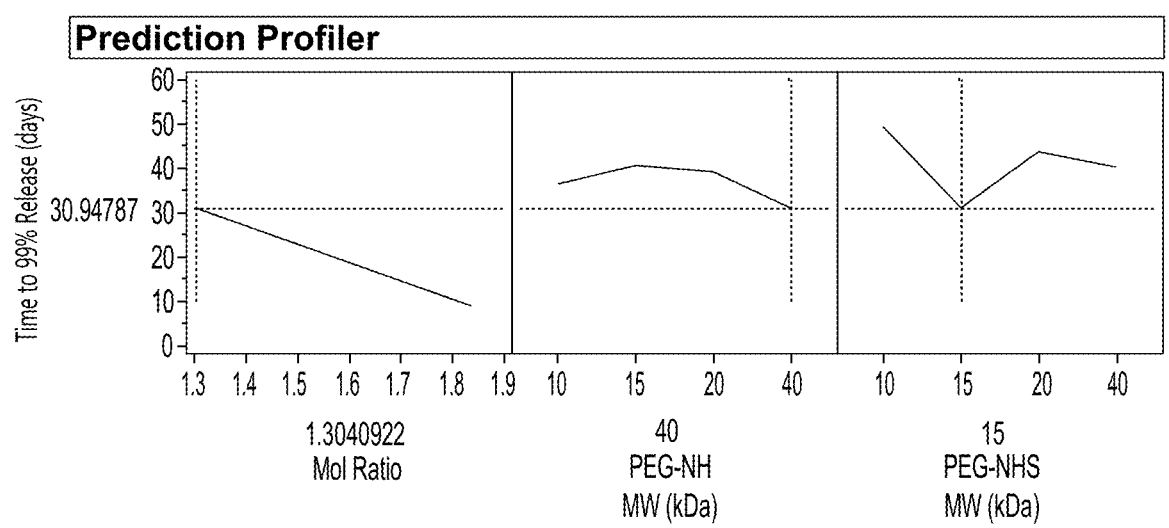
FIG. 20 is a graph showing that, in accordance with the predictive model, a combination of a molar ratio of 1.30, PEG-NH MW of 40 kDa, and PEG-NHS MW of 15 kDa can produce a hydrogel with a release period of 30.9 days for 99% release.
Figure 21:
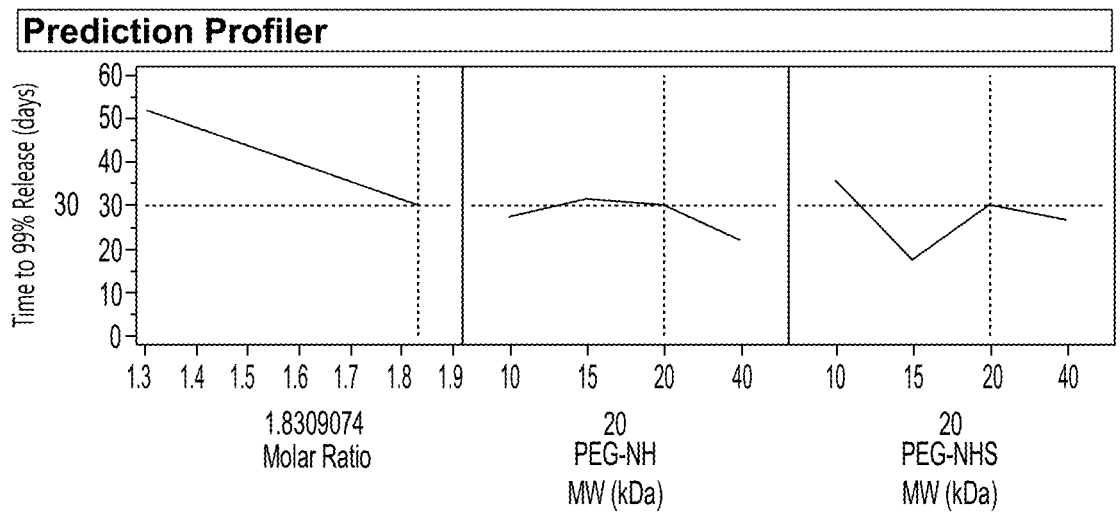
FIG. 21 is a graph showing that, in accordance with the predictive model, a combination of a molar ratio of 1.83, PEG-NH MW of 20 kDa, and PEG-NHS MW of 20 kDa can produce a hydrogel with a release period of 30 days for 99% release.
Figure 22:
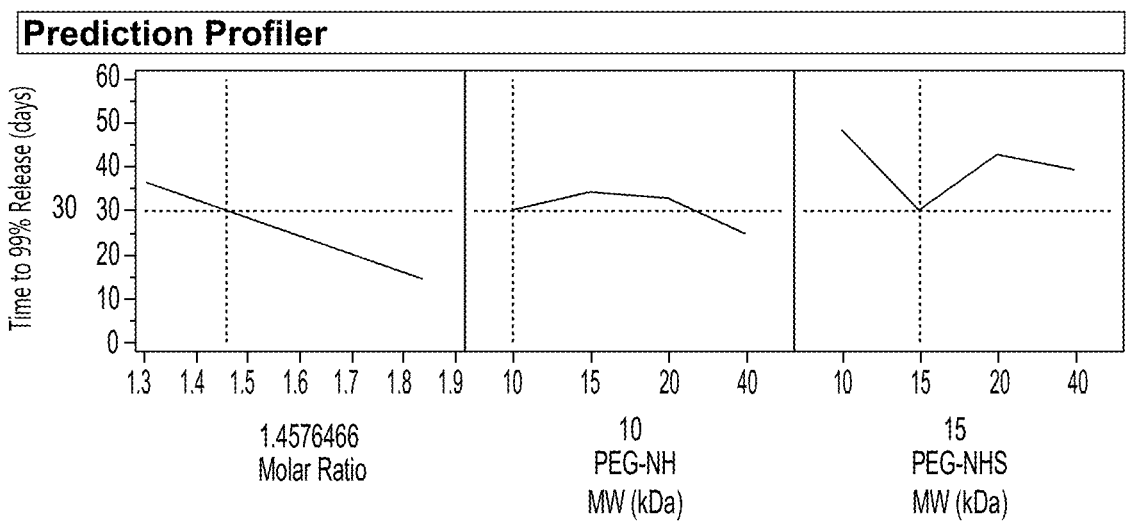
FIG. 22 is a graph showing that, in accordance with the predictive model, a combination of a molar ratio of 1.46, PEG-NH MW of 10 kDa, and PEG-NHS MW of 15 kDa can produce a hydrogel with a release period of 30 days for 99% release.

FIG. 9 shows an example of tuning factors to counteract impact of change in form factor from slab to microparticles on release kinetics. Microparticles are produced via milling and sieving and are non-uniform. The goal is to reduce burst release and achieve 45-56 days release.

Example 2

This example investigates the impact of three factors on the release profile of the hydrogel: molar ratio of NH:NHS, molecular weight of PEG-NH, and molecular weight of PEG-NHS. Molar ratios are chosen to be >1.0 and range 1.3-1.8 to meet target duration <60 days. Commercially available 4-arm PEG NH and NHS groups are included in the study. The molar ratio is treated as a continuous factor, while the molecular weight of PEG-NH or PEG-NHS is treated categorically. See Table 7 for design parameters.

TABLE 7

Design Parameters

| Factor Name | Role | Values | | | |
|---|---|---|---|---|---|
| Molar Ratio (NH:NHS) | Continuous | 1.3 | | 1.8 | |
| PEG-NH MW (4-arm) | Categorical | 10 kDa | 15 kDa | 20 kDa | 40 kDa |
| PEG-NHS MW (4-arm) | Categorical | 10 kDa | 15 kDa | 20 kDa | 40 kDa |

In Table 7, constant parameters: 50% protein loading (mAb IgG1), 60% solid loading, and SA:V ~23 mm$^{-1}$.

Table 8 below shows the different runs performed to produce the predictive model.

TABLE 8

| Run # | Molar Ratio | PEG NH Reagent (kDa) | PEG NHS Reagent (kDa) |
|---|---|---|---|
| 1 | 1.8 | 10 | 15 |
| 2 | 1.3 | 10 | 20 |
| 3 | 1.8 | 15 | 20 |
| 4 | 1.3 | 15 | 15 |

TABLE 8-continued

| Run # | Molar Ratio | PEG NH Reagent (kDa) | PEG NHS Reagent (kDa) |
|---|---|---|---|
| 5 | 1.3 | 20 | 20 |
| 6 | 1.3 | 20 | 10 |
| 7 | 1.3 | 40 | 40 |
| 8 | 1.8 | 40 | 15 |
| 9 | 1.8 | 40 | 10 |
| 10 | 1.6 | 10 | 15 |
| 11 | 1.6 | 20 | 10 |
| 12 | 1.6 | 20 | 40 |
| 13 | 1.6 | 40 | 40 |

FIG. 10 shows the model analysis. Power >0.95 with AC<6 indicate strong predictive power of model.

TABLE 9

Example Parameter Tuning Capabilities

| PEG-NH MW (kDa) | PEG-NHS MW (kDa) | Molar ratio range | Release range (Time to 99% Release) |
|---|---|---|---|
| 10 | 15 | 1.3-1.8 | 9-31 days |
| 40 | 20 | 1.3-1.8 | 22-44 days |
| 15 | 10 | 1.3-1.8 | 37-59 days |

As shown in Table 10 below, the accuracy of the model for the four selected points is >99.8%. Overall accuracy of prediction equation is >99.9% in this example formulation. Prediction Accuracy (i.e. R-squared) for all fits of formulations used in the model is >98%.

TABLE 10

Prediction Model Closely Matches Experimental Data

| % Release | Time (days) - measured | Time (days) - predicted | Bias (days) |
|---|---|---|---|
| 23.3 | 30.9 | 31.3 | −0.4 |
| 51.5 | 42.0 | 41.7 | −0.3 |
| 72.5 | 45.0 | 45.1 | −0.1 |
| 99.7 | 49.0 | 49.0 | 0 |

Table 11 summarizes the 4-arm XPEG formulations using varying molar ratio, PEG NH molecular weight, and PEG NHS molecular weight with constant protein (IgG1 mAb1), excipient loading, and surface area:volume (SA:V) ratio to achieve specified release period <60 days.

TABLE 11

| Release Period (days) | PEG NH MW (kDa) | PEG NHS MW (kDa) | Molar Ratio (NH:NHS) | Solid Loading (% w/w) |
|---|---|---|---|---|
| 9 | 40 | 15 | 1.83 | 60 |
| 14 | 40 | 15 | 1.71 | 60 |
| 21 | 40 | 15 | 1.54 | 60 |
| 21 | 10 | 15 | 1.67 | 60 |
| 30 | 20 | 20 | 1.83 | 60 |
| 30 | 40 | 15 | 1.46 | 60 |
| 58 | 15 | 10 | 1.30 | 60 |

Example 3

Table 12 shows that solvent mixture combinations and ratios can be adjusted to alter XPEG reaction time to enable scale-up manufacturing. Reaction time is defined as the time from initial mixing of solvent/PEG solutions to time when hydrogel becomes a monolithic, solid structure.

TABLE 12

| Solvent A | Solvent B | % v/v Mixture of Solvents A and B | mg/mL PEG Reagent in Solvent A/B | Reaction Time (seconds) |
| --- | --- | --- | --- | --- |
| Methylene Chloride (DCM) | Ethyl Acetate (EA) | 90% DCM 10% EA | 15 | 95 |
| Methylene Chloride (DCM) | Ethyl Acetate (EA) | 50% DCM 50% EA | 15 | 113 |
| Methylene Chloride (DCM) | N/A | 100% DCM | 15 | 120 |
| Methylene Chloride (DCM) | Chloroform (Chl) | 90% DCM 10% Chl | 15 | 143 |
| Methylene Chloride (DCM) | Chloroform (Chl) | 50% DCM 50% Chl | 15 | 159 |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of producing a hydrogel having a biologic and excipient disposed therein with a desired release profile for the biologic, wherein the biologic and excipient is in a solid state formulation prior to being disposed in the hydrogel, wherein the hydrogel is characterized by a desired release period of about one week to about six months for at least 90% biologic release, the method comprising:
   predetermining a weight ratio of the biologic and excipient to the hydrogel in the range of 60% to 90%,
   predetermining at least one of the following parameters:
      (a) the number of nucleophilic groups in a first precursor;
      (b) the number of electrophilic groups in a second precursor;
      (c) the molecular weight of the first precursor;
      (d) the molecular weight of the second precursor;
      (e) a weight percentage of the biologic in the solid state formulation; and
      (f) a ratio of surface area to volume of the hydrogel;
   determining a molar ratio of the total number of moles of the nucleophilic group to the total number of moles of the electrophilic group alone, or in combination with any one or more of the above parameters that is not predetermined, until the desired release profile is achieved, wherein the molar ratio of the nucleophilic group to the electrophilic group is in the range of 1.1 to 2; and
   crosslinking the first precursor and the second precursor at the determined molar ratio around the solid state formulation under anhydrous conditions.

2. The method of claim 1, wherein the molar ratio of the total number of moles of the nucleophilic group to the total number of moles of the electrophilic group is in the range of 1.5 to 2.0.

3. The method of claim 1, wherein the molar ratio of the total number of moles of the nucleophilic group to the total number of moles of the electrophilic group is in the range of 1.3 to 1.8.

4. The method of claim 1, wherein the biologic is a recombinant protein.

5. The method of claim 4, wherein the recombinant protein is an antibody or a Trap protein (a fusion protein with decoy receptor domains).

6. The method of claim 1, wherein the nucleophilic group comprises a primary amine or a primary thiol.

7. The method of claim 1, wherein the electrophilic group comprises succinimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole.

8. The method of claim 1, wherein the number of the nucleophilic groups in the first precursor is in the range of about 2 to about 10.

9. The method of claim 1, wherein the number of the electrophilic groups in the second precursor is in the range of about 2 to about 10.

10. The method of claim 1, wherein the weight percentage of the biologic in the solid state formulation is between about 30% to about 95%.

11. The method of claim 1, wherein the desired release profile comprises:
   (a) a release period of about two months to six months for at least 90% biologic release;
   (b) a release period of about one week to two months for at least 90% biologic release;
   (c) near-linear release of the biologic over at least one week;
   (d) a delayed-release portion;
   (e) a sigmoidal shape;
   (f) a linear portion;
   (g) a near-linear portion;
   (h) a logarithmic portion;
   (i) an exponential portion;
   or a combination thereof.

12. The method of claim 1, wherein the crosslinking occurs in the presence of an organic solvent that is anhydrous and hydrophobic.

13. The method of claim 12, wherein the organic solvent is methylene chloride, ethyl acetate, dimethyl carbonate, chloroform, or a combination thereof.

14. The method of claim 1, wherein the determining step is performed with a predictive model.

15. The method of claim 14, wherein the molar ratio has a continuous effect on release profile in the predictive model.

16. The method of claim 14, wherein the molecular weights of the first and second precursors have a non-continuous effect on release profile in the predictive model.

17. A method of producing a hydrogel having a biologic and excipient disposed therein, wherein the biologic and excipient is in a solid state formulation prior to being disposed in the hydrogel, and wherein the hydrogel is characterized by a desired release period of about one week to about six months for at least 90% biologic release, the method comprising:
   selecting a first precursor that comprises two or more nucleophilic groups, wherein the first precursor has a molecular weight in the range of about 1 kDa to about 100 kDa;

selecting a second precursor that comprises two or more electrophilic groups, wherein the second precursor has a molecular weight in the range of about 1 kDa to about 100 kDa;

selecting a weight ratio of the biological and excipient to the hydrogel in the in the range of 60% to 90%;

determining at least one of the following parameters alone, or in combination, until the desired release period is achieved:

(a) a molar ratio of the total number of moles of the nucleophilic group to the total number of moles of the electrophilic group;

(b) a weight percentage of the biologic in the solid state formulation; and (c) a ratio of surface area to volume of the hydrogel; and crosslinking the first precursor and the second precursor at the determined molar ratio around the solid state formulation under anhydrous conditions, wherein the molar ratio of the total number of moles of the nucleophilic group to the total number of moles of the electrophilic group is in the range of 1.1 to 2.

18. The method of claim 17, wherein the molar ratio of the total number of moles of the nucleophilic group to the total number of moles of the electrophilic group is in the range of 1.5 to 2.0.

19. The method of claim 17, wherein the molar ratio of the total number of moles of the nucleophilic group to the total number of moles of the electrophilic group is in the range of 1.3 to 1.8.

20. The method of claim 17, wherein the biologic is a recombinant protein.

21. The method of claim 20, wherein the recombinant protein is an antibody or a Trap protein (a fusion protein with decoy receptor domains).

22. The method of claim 17, wherein the nucleophilic group comprises a primary amine or a primary thiol.

23. The method of claim 17, wherein the electrophilic group comprises succinimide, succinimide ester, n-hydroxysuccinimide, maleimide, succinate, nitrophenyl carbonate, aldehyde, vinylsulfone, azide, hydrazide, isocyanate, diisocyanate, tosyl, tresyl, or carbonyldiimidazole.

24. The method of claim 17, wherein the first precursor comprises about 2 to about 10 nucleophilic groups.

25. The method of claim 17, wherein the second precursor comprises about 2 to about 10 electrophilic groups.

26. The method of claim 17, wherein the weight percentage of the biologic in the solid state formulation is between about 30% to about 95%.

27. The method of claim 17, wherein the desired release period comprises:

(a) a release period of about two months to six months for at least 90% biologic release;

(b) a release period of about one week to two months for at least 90% biologic release;

(c) near-linear release of the biologic;

(d) a delayed-release portion;

(e) a sigmoidal shape;

(f) a linear portion;

(g) a near-linear portion;

(h) a logarithmic portion;

(i) an exponential portion;

or a combination thereof.

28. The method of claim 17, wherein the crosslinking occurs in the presence of an organic solvent that is anhydrous and hydrophobic.

29. The method of claim 28, wherein the organic solvent is methylene chloride, ethyl acetate, dimethyl carbonate, chloroform, or a combination thereof.

30. The method of claim 17, wherein the determining step is performed with a predictive model.

31. The method of claim 30, wherein the molar ratio has a continuous effect on release period in the predictive model.

32. The method of claim 30, wherein the molecular weights of the first and second precursors have a non-continuous effect on release period in the predictive model.

* * * * *